(12) United States Patent
Dacey

(10) Patent No.: US 9,265,578 B2
(45) Date of Patent: Feb. 23, 2016

(54) MULTI-COMPONENT PACKAGES FOR MEDICAL DEVICES

(71) Applicant: Ethicon, Inc., Somerville, NJ (US)

(72) Inventor: Denise Marie Dacey, Glen Gardner, NJ (US)

(73) Assignee: Ethicon, LLC, San Lorenzo, PR (US)

( * ) Notice: Subject to any disclaimer, the term of this patent is extended or adjusted under 35 U.S.C. 154(b) by 11 days.

(21) Appl. No.: 14/071,310

(22) Filed: Nov. 4, 2013

(65) Prior Publication Data

US 2015/0122681 A1    May 7, 2015

(51) Int. Cl.
*B65D 83/10* (2006.01)
*A61B 19/02* (2006.01)

(52) U.S. Cl.
CPC ............... *A61B 19/02* (2013.01); *A61B 19/026* (2013.01); *A61B 19/0271* (2013.01); *A61B 2019/0213* (2013.01); *A61B 2019/0222* (2013.01); *A61B 2019/0267* (2013.01)

(58) Field of Classification Search
CPC ...... A61B 19/02; B65D 1/36; B65D 73/0092; B65D 75/368; B65D 75/379; B65D 75/329; B65D 75/362; B65D 75/324; B65D 75/366
See application file for complete search history.

(56) References Cited

U.S. PATENT DOCUMENTS

| | | | |
|---|---|---|---|
| 3,724,651 A | 4/1973 | Link | |
| 3,926,309 A | 12/1975 | Center | |
| 3,985,289 A * | 10/1976 | Prince | ...................... 229/125.08 |
| 4,206,844 A | 6/1980 | Thukamoto et al. | |
| 4,332,322 A | 6/1982 | Jaeschke et al. | |
| 4,511,035 A | 4/1985 | Alpern | |
| D282,482 S | 2/1986 | Anderson | |
| D282,684 S | 2/1986 | Cline | |
| 4,844,251 A | 7/1989 | Gueret | |
| 5,031,775 A | 7/1991 | Kane | |
| 5,098,391 A | 3/1992 | Pantages et al. | |
| 5,106,662 A | 4/1992 | Khayat | |
| 5,165,540 A * | 11/1992 | Forney | .......................... 206/364 |

(Continued)

FOREIGN PATENT DOCUMENTS

| | | |
|---|---|---|
| EP | 0440427 | 6/1994 |
| EP | 0664991 | 8/1995 |
| WO | 2008033874 | 3/2008 |

OTHER PUBLICATIONS

International Search Report issued in corresponding International application No. PCT/US2014/062412, mailed Feb. 4, 2015, 4 pages.

*Primary Examiner* — Anthony Stashick
*Assistant Examiner* — James Way
(74) *Attorney, Agent, or Firm* — Doherty IP Law Group LLC

(57) ABSTRACT

A package for a medical device includes a tray having elements that receive a medical device. The tray has proximal retainer posts for limiting proximal movement of the medical device relative to the tray. The package includes a retainer lid secured to the tray for covering the top surface of the tray at the distal end of the tray, and a retainer sleeve that is wrapped around the top and bottom surfaces of the tray and secured to the tray by the retainer lid. The proximal end of the retainer sleeve includes a top panel that covers the top surface of the tray at the proximal end of the tray. The top panel of the retainer sleeve has a free edge that is adapted to flex away from the top surface of said tray so that the medical device can be grasped.

22 Claims, 33 Drawing Sheets

(56) References Cited

U.S. PATENT DOCUMENTS

| | | |
|---|---|---|
| 5,226,535 A | 7/1993 | Rosdhy et al. |
| 5,234,106 A | 8/1993 | Transue et al. |
| 5,284,244 A * | 2/1994 | O'Toole et al. ............... 206/363 |
| 5,351,822 A | 10/1994 | Sinn |
| 5,353,929 A | 10/1994 | Foster |
| 5,358,624 A | 10/1994 | Roshdy et al. |
| 5,375,717 A | 12/1994 | Roshdy |
| D356,677 S | 3/1995 | Kalasountas |
| 5,447,230 A * | 9/1995 | Gerondale ............... 206/363 |
| 5,447,231 A | 9/1995 | Kastenhofer |
| 5,487,469 A | 1/1996 | Roshdy et al. |
| 5,497,601 A | 3/1996 | Gonzalez |
| 5,498,242 A | 3/1996 | Cooke |
| 5,501,341 A | 3/1996 | Van Es |
| 5,601,189 A | 2/1997 | Roshdy |
| 5,655,657 A | 8/1997 | Roshdy |
| 5,699,909 A | 12/1997 | Foster |
| D395,359 S | 6/1998 | Olsen |
| 5,788,063 A | 8/1998 | Van Ness |
| 5,842,567 A | 12/1998 | Rowe |
| 5,878,549 A | 3/1999 | Littmann et al. |
| 5,888,565 A * | 3/1999 | Gics ............... 426/124 |
| D411,948 S | 7/1999 | Chipperfield |
| 5,972,008 A | 10/1999 | Kalinski et al. |
| 6,047,826 A | 4/2000 | Kalinski |
| 6,261,616 B1 * | 7/2001 | Simpson et al. ............... 426/119 |
| 6,308,875 B1 | 10/2001 | Almo |
| 6,425,900 B1 | 7/2002 | Knodel et al. |
| 6,779,701 B2 | 8/2004 | Bailly et al. |
| 6,814,236 B2 * | 11/2004 | Roshdy ............... 206/570 |
| 6,889,839 B1 * | 5/2005 | Rosten et al. ............... 206/583 |
| 6,986,730 B1 | 1/2006 | Hoekstra |
| 6,994,213 B2 | 2/2006 | Girard, Jr. et al. |
| D541,933 S | 5/2007 | White et a |
| D542,525 S | 5/2007 | Schmidt |
| 7,247,329 B2 | 7/2007 | Mattisson |
| 7,255,230 B1 * | 8/2007 | Appelbaum ............... 206/463 |
| 7,281,630 B2 * | 10/2007 | Hartman et al. ............... 206/467 |
| D562,549 S | 2/2008 | Bodnar |
| D576,275 S | 9/2008 | White et al. |
| D578,642 S | 10/2008 | White et al. |
| D590,246 S | 4/2009 | Kirk et al. |
| D641,466 S | 7/2011 | Merboth et al. |
| 8,292,076 B2 | 10/2012 | Dacey |
| 8,413,810 B2 | 4/2013 | Merboth et al. |
| 2002/0165549 A1 | 11/2002 | Owusu-Akyaw |
| 2003/0121821 A1 | 7/2003 | Roshdy |
| 2005/0077197 A1 * | 4/2005 | Detruit et al. ............... 206/363 |
| 2005/0092636 A1 | 5/2005 | Su-Syin |
| 2005/0189252 A1 | 9/2005 | Naylor et al. |
| 2010/0292710 A1 | 11/2010 | Daniel et al. |
| 2010/0292712 A1 | 11/2010 | Nering et al. |
| 2010/0292713 A1 | 11/2010 | Cohn et al. |
| 2010/0292715 A1 | 11/2010 | Nering et al. |
| 2010/0327042 A1 | 12/2010 | Amid et al. |
| 2012/0061262 A1 | 3/2012 | Merboth et al. |
| 2012/0175401 A1 | 7/2012 | Bachman |

* cited by examiner

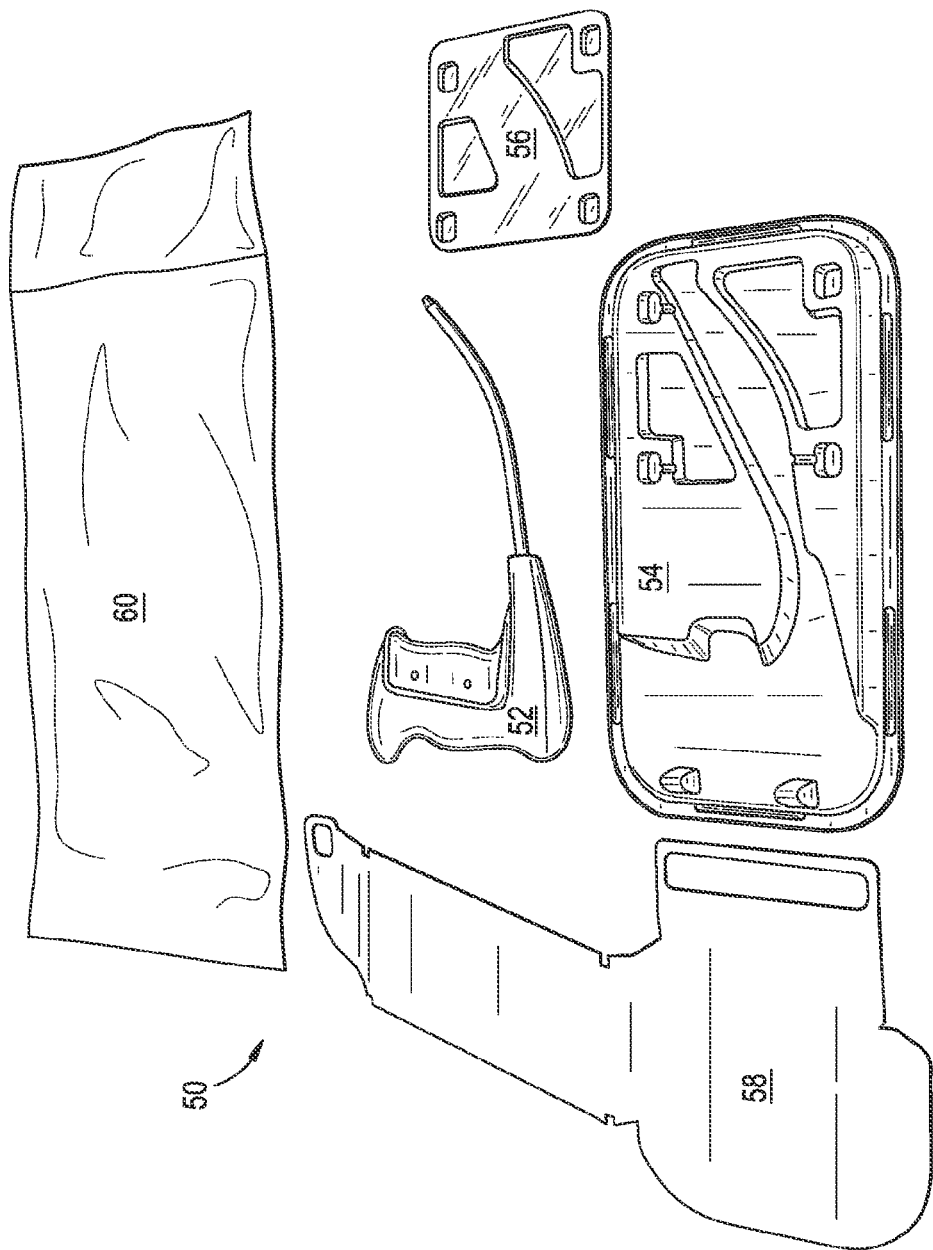

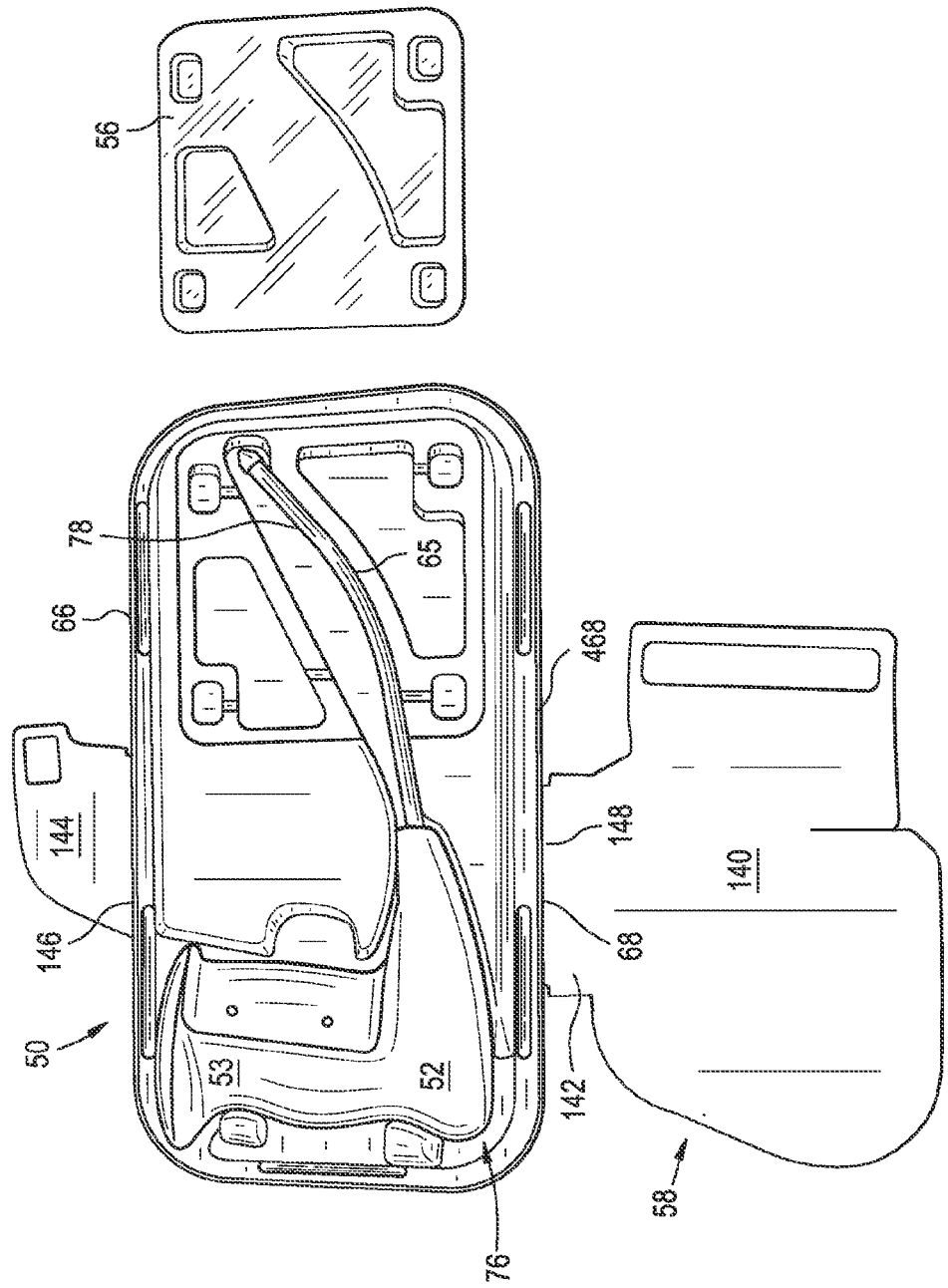

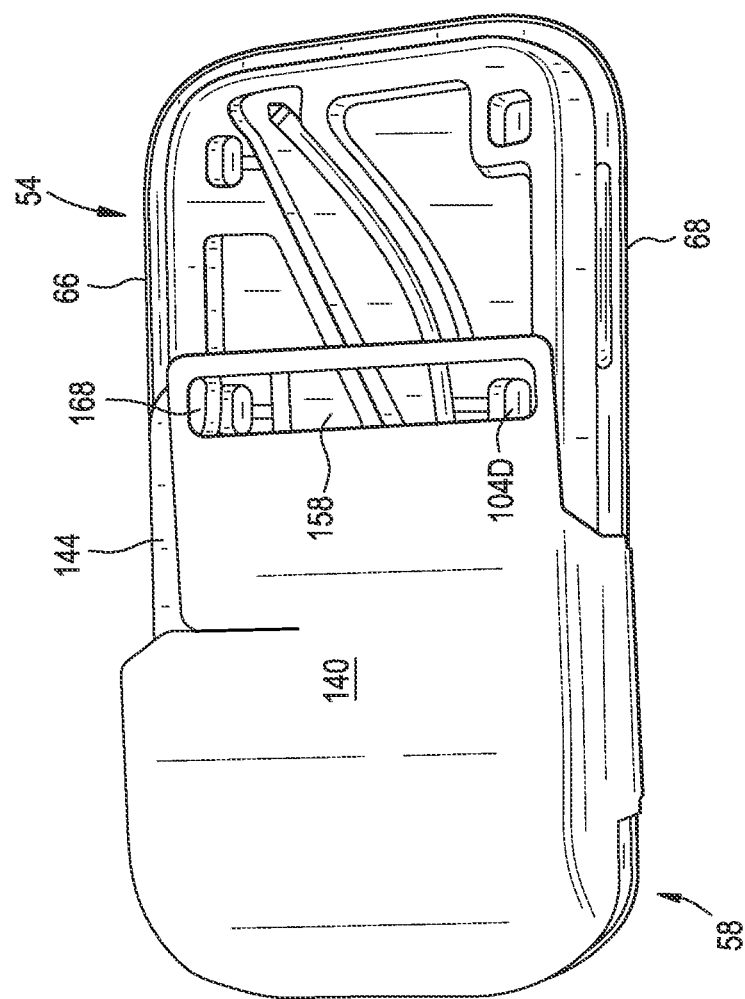

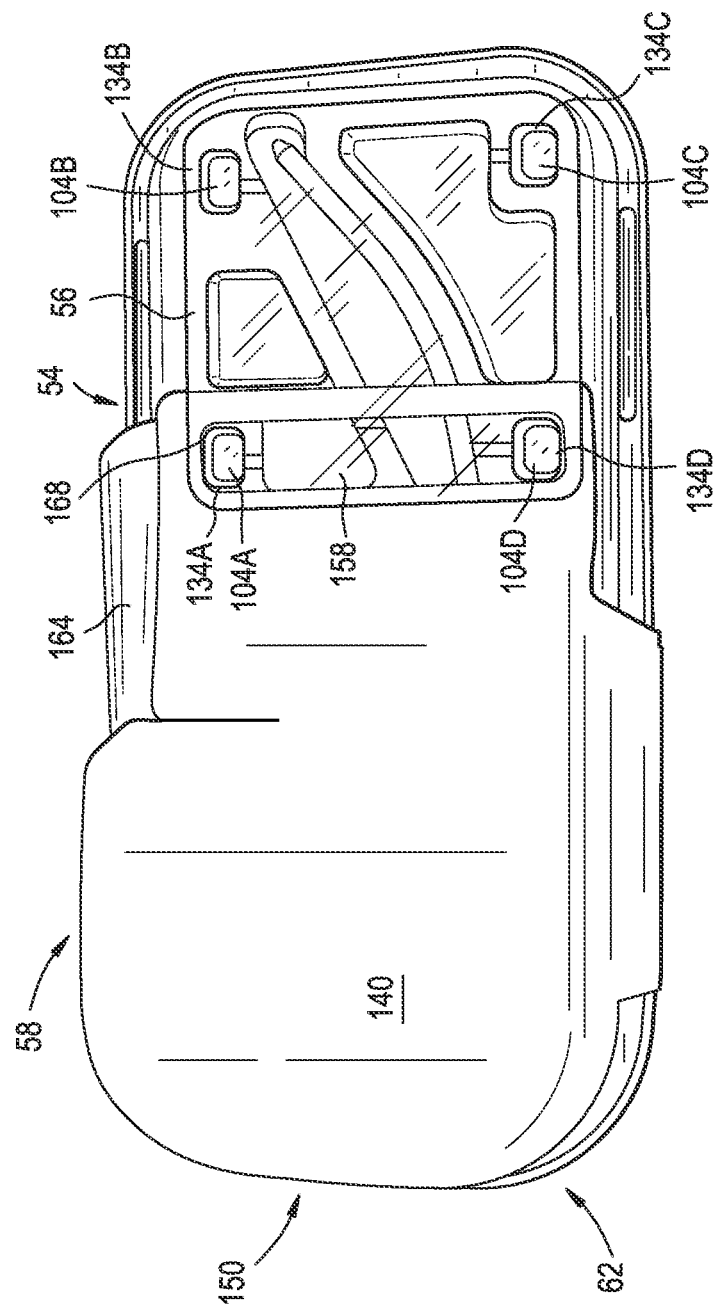

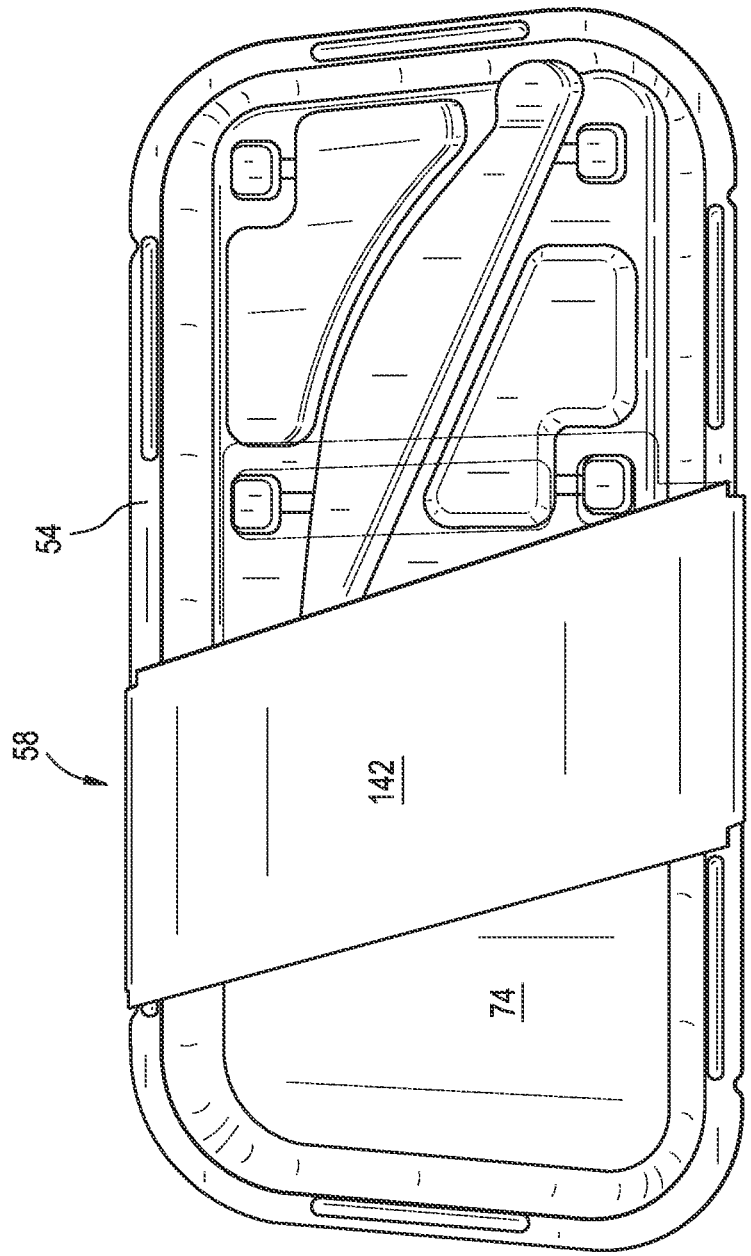

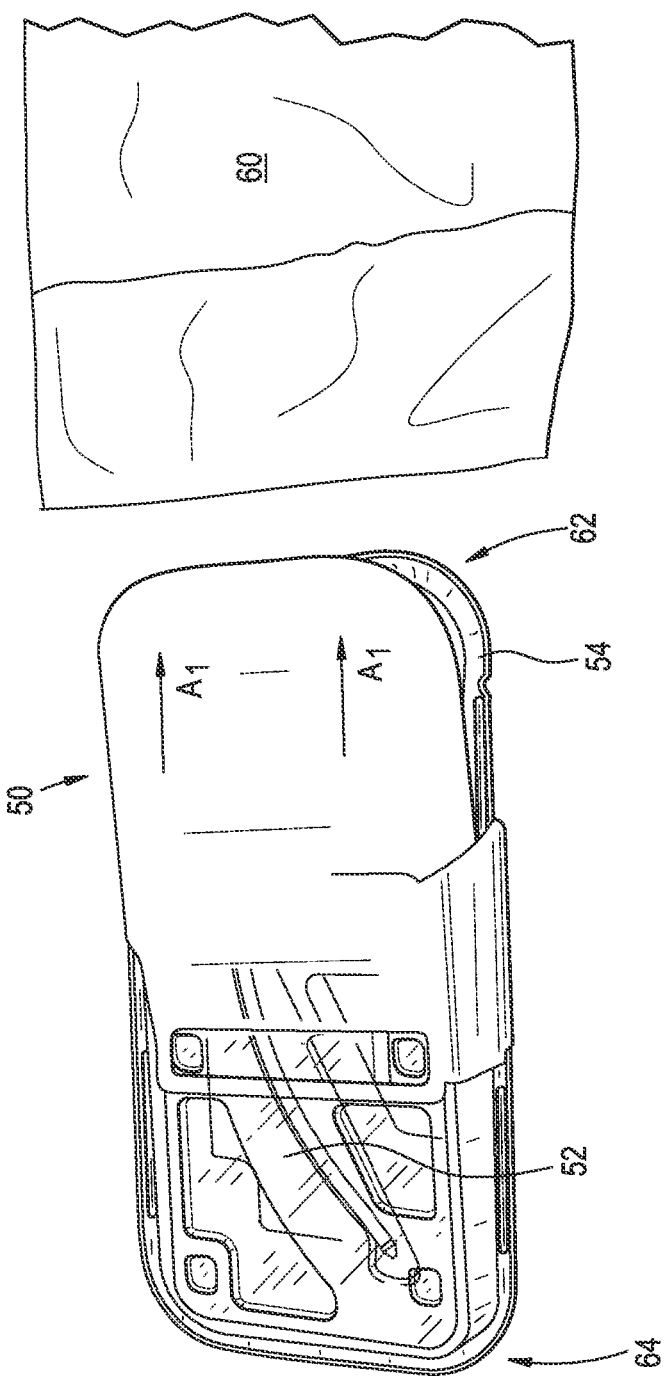

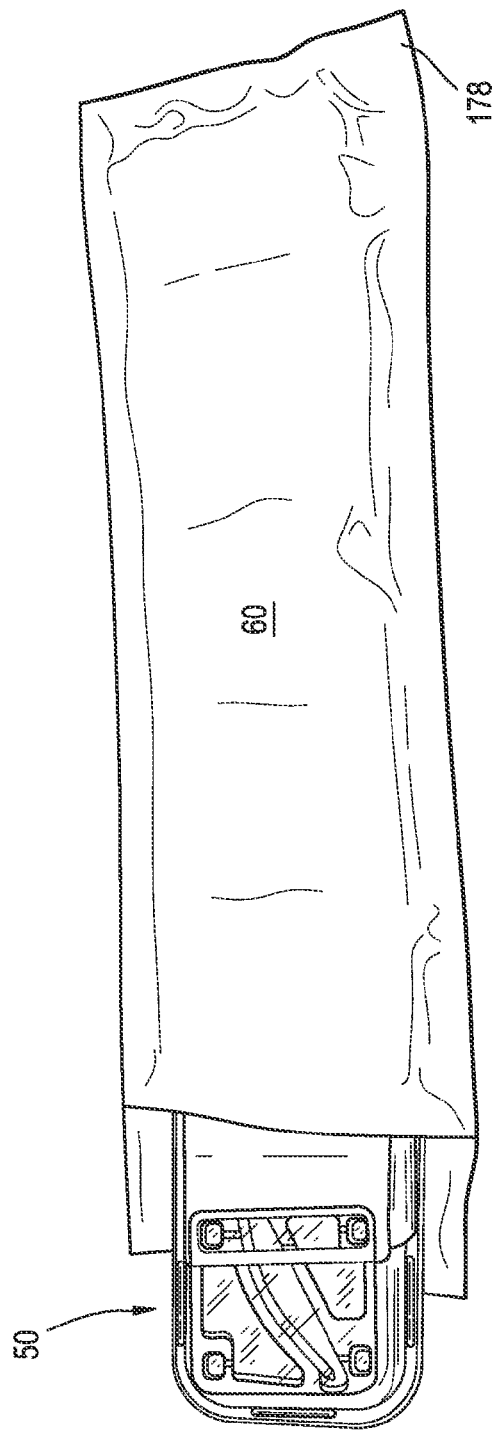

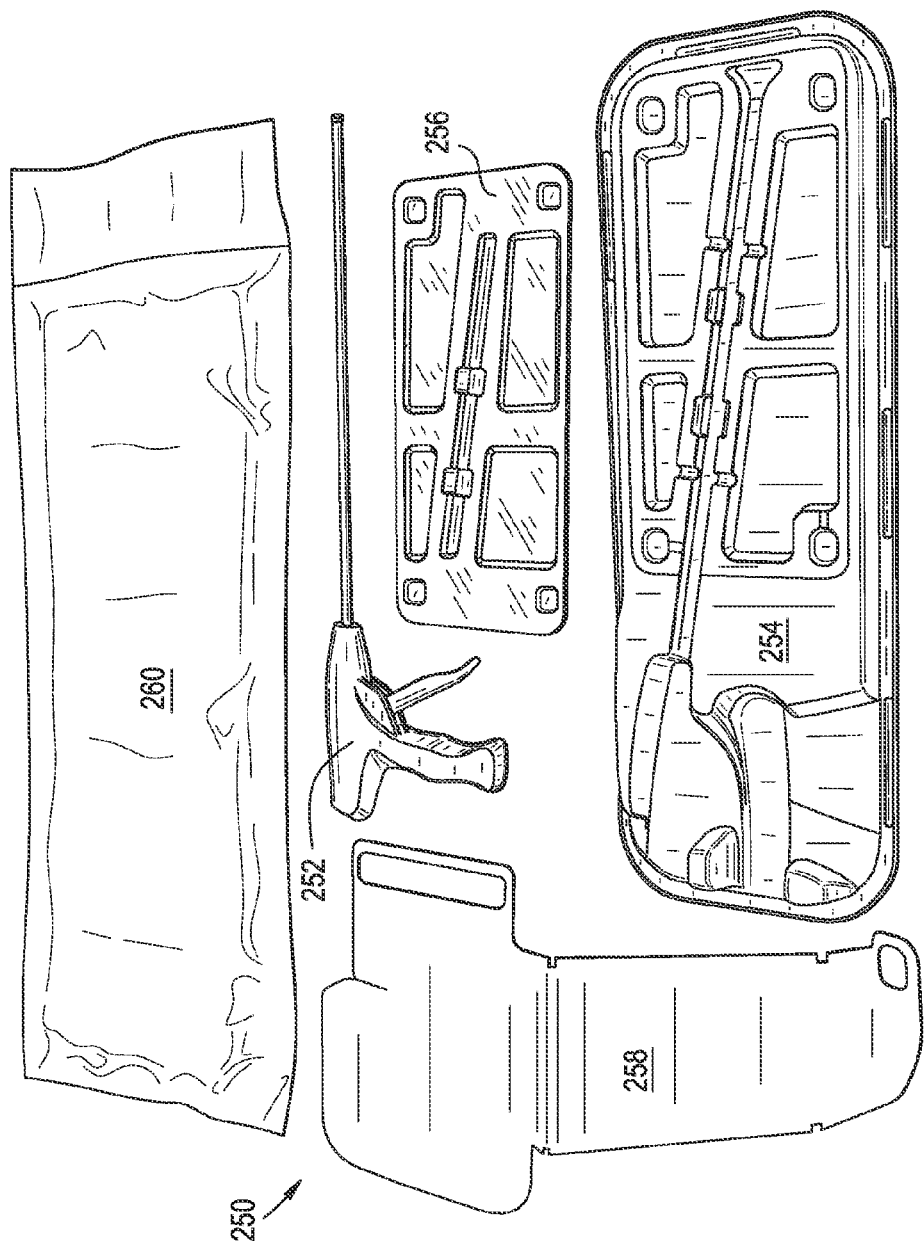

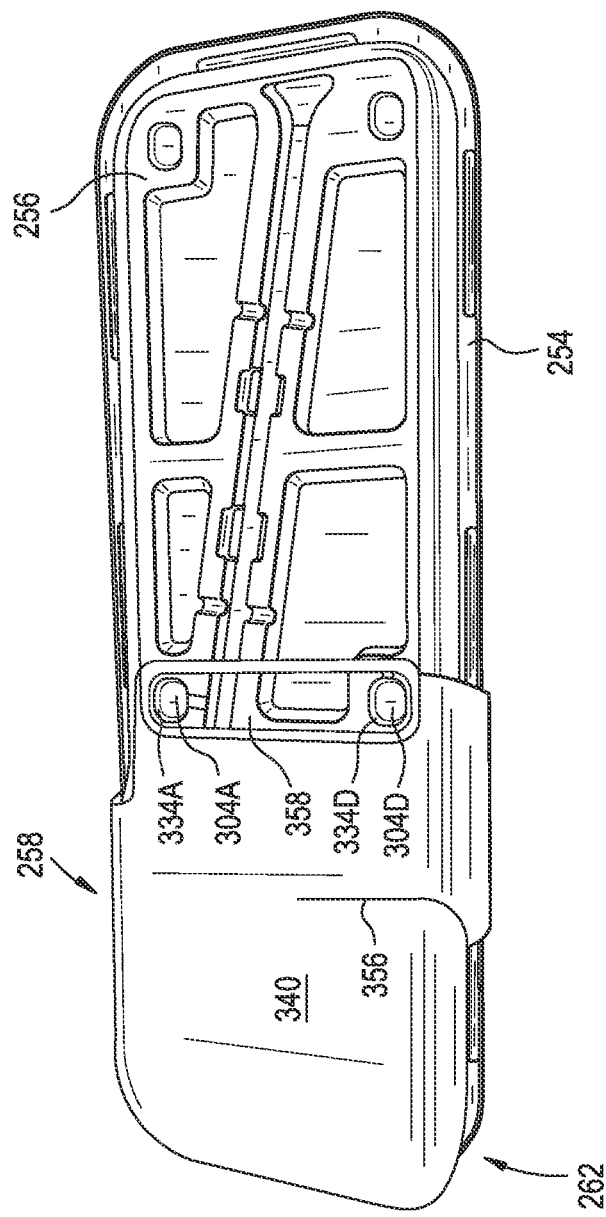

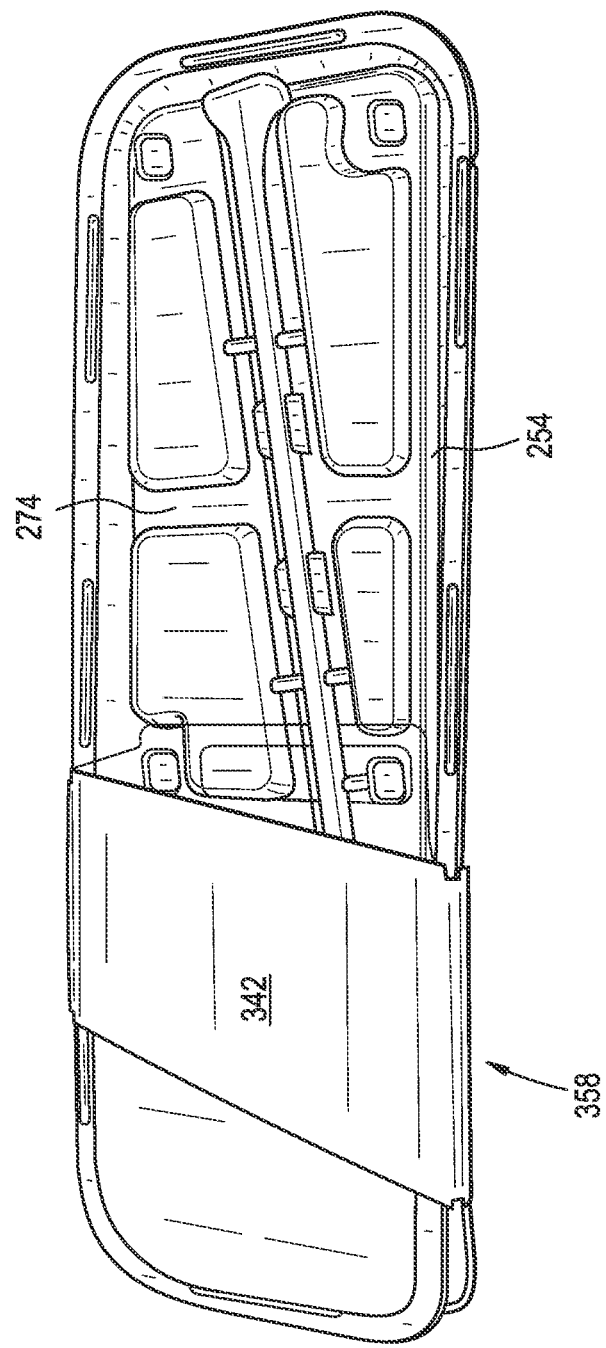

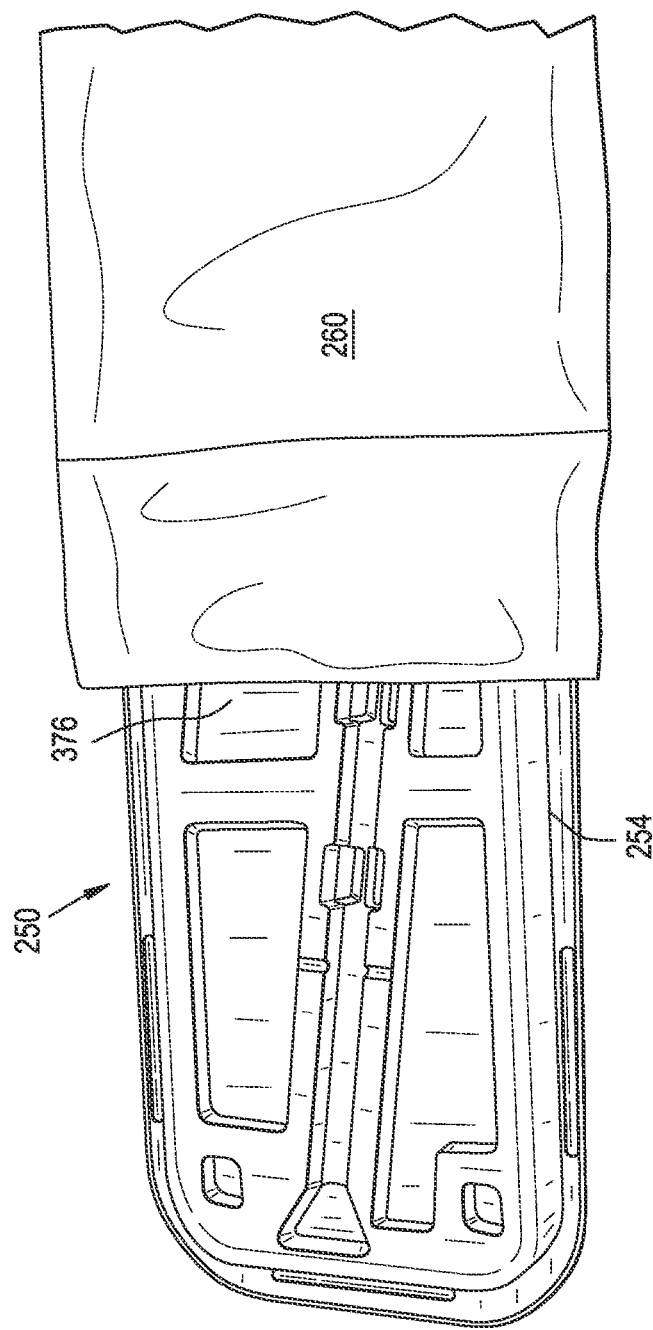

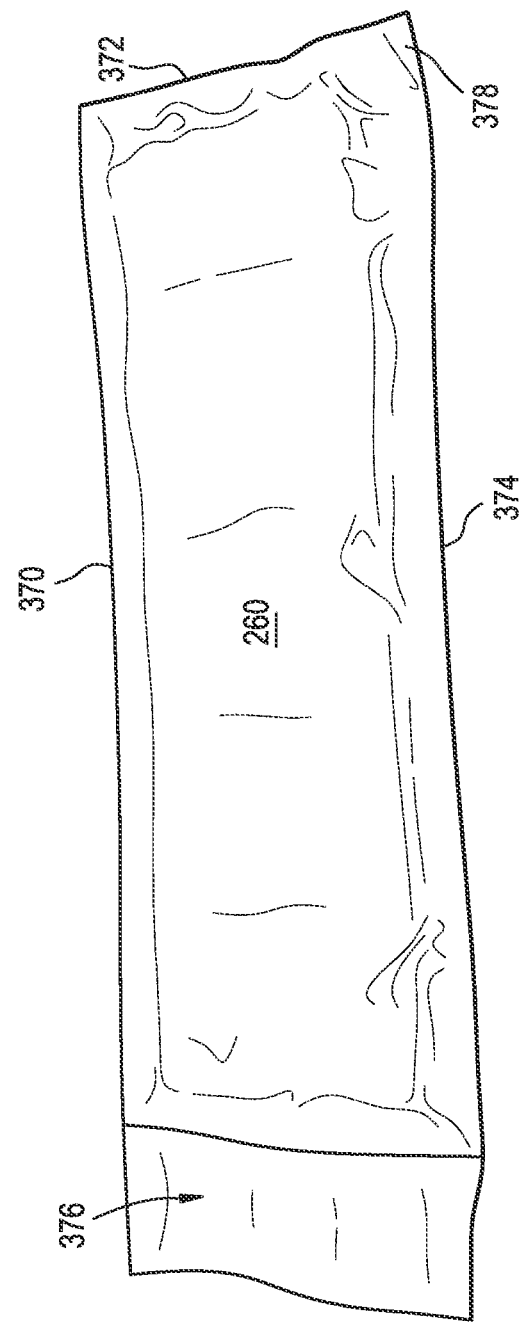

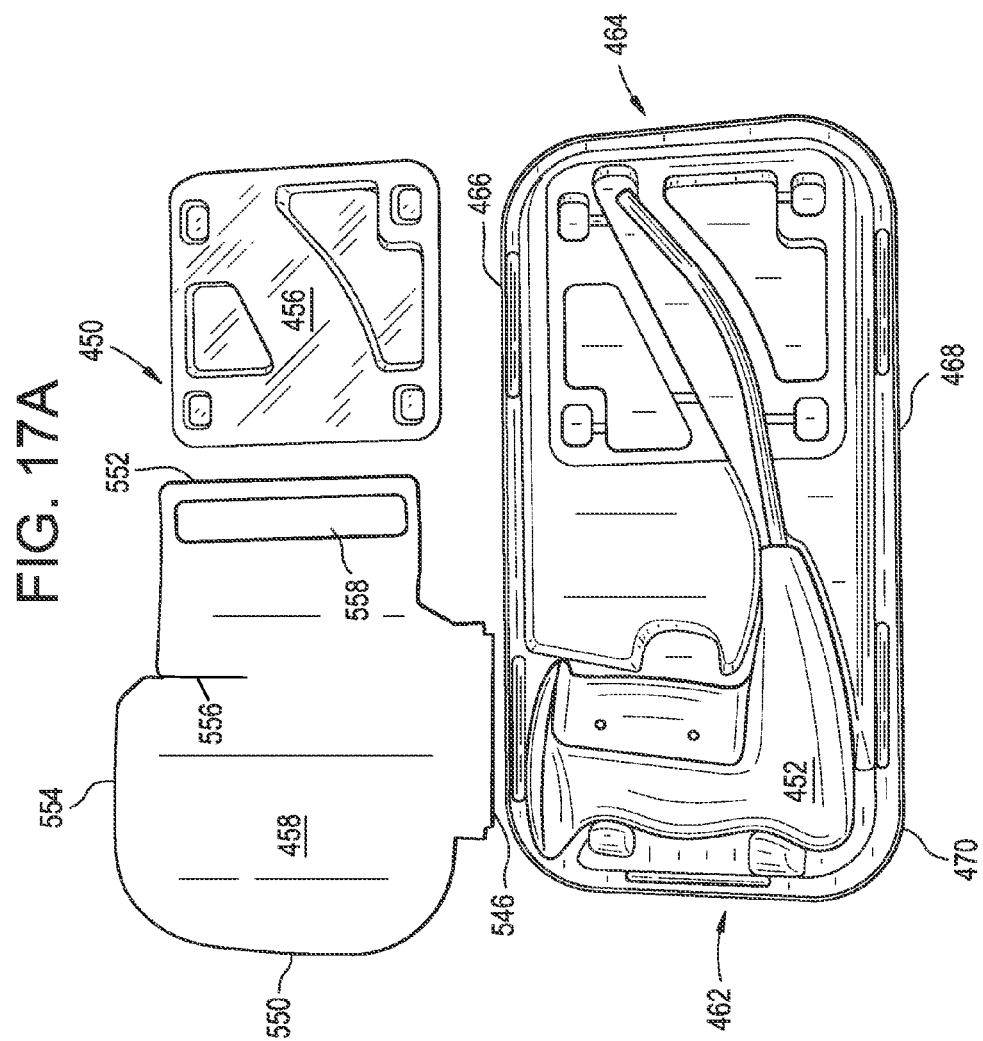

MULTI-COMPONENT PACKAGES FOR MEDICAL DEVICES

BACKGROUND OF THE INVENTION

1. Field of the Invention

The present invention is generally related to medical devices, and is more specifically related to packages for medical devices.

2. Description of the Related Art

During surgical procedures, great care is taken to prevent contamination of the medical devices that are used during operations. An operating team typically includes at least one member whose primary function is to open packages containing medical devices and to present the medical devices to a sterile nurse or surgeon in a manner that maintains the medical devices in a sterile condition.

A number of factors must be considered when designing packages for medical devices. First, the package must properly surround and protect the medical device from damage. Second, the packaging materials must be chosen to accommodate the sterilization process that will be used for the medical device. In addition, the package must be easy to open to enable efficient access of the medical device during a surgical procedure.

Packages for medical devices are also subject to considerations such as the cost of the materials, the cost and complexity of tooling to make the package, ease of package assembly, and ease of manufacture and shipping both the empty package and after the components are assembled together. An increasingly competitive economic environment exacerbates these sometimes competing considerations so that safety and efficacy must be achieved while costs are minimized.

It is particularly challenging to package elongated, bulky and/or relatively heavy medical devices. One solution is disclosed in commonly assigned U.S. Pat. No. 5,375,717 to Roshdy, which discloses a foldable package made from a sheet of cut and folded paperboard material. The package is used to retain an endoscope introducer and an instrument that is used with the endoscope introducer. The foldable package has openings and flaps that retain both the proximal and distal ends of the introducer. A proximal flap overlies the introducer. The proximal flap is used to release the package and expose the introducer, permitting the endoscope introducer to be removed from the package in one smooth motion.

Other efforts have been directed to providing packages for medical devices that allow for efficient opening of the package and presentation of the medical devices to surgical personnel in a sterile condition. One type of package provides a color-marked envelope that indicates the area to be torn off to provide an access opening to the contents within the envelope without affecting the sterility of the contents. Another type of package provides a tear string that may be pulled to open the envelope so that the contents may be removed using forceps or similar tools.

Commonly assigned U.S. Pat. No. 8,292,076 to Dacey et al. discloses sealed pouches for medical devices. In one embodiment, a sealed pouch includes first and second foil sheets having opposing inner surfaces that are joined together by a seal for defining a sealed area of the pouch located inside the seal and an unsealed area of the pouch located outside the seal. The sealed pouch includes a textured opening flange located adjacent an edge of the pouch for peeling the first and second foil sheets away from one another for breaking the seal and opening the sealed pouch. The textured opening flange is located within the unsealed area of the pouch and includes at least one roughened surface formed on at least one of the first and second foil sheets. A leg of the seal passes through the textured opening flange. The roughened surface on the textured opening flange makes it easier to break the leg of the seal for pulling the foil sheets apart.

In spite of the above advances in medical device packaging, there remains a need for improved packages for medical devices that are easy to open and that ensure the maintenance of strong seals prior to opening for maintaining a sterile environment inside the packages. There also remains a need for packages that ensure that the medical devices are held securely in place to avoid damage to the devices and/or the sealed outer pouches. There also remains a need for packages for medical devices that minimize the level of stress exerted upon the sealed outer pouches during loading, sterilization, shipping, and handling. In addition, there remains a need for packages whereby the medical devices may be easily removed from the packages without requiring partial or full disassembly of the packages. There also remains a need for packages that provide a clear indication of the end of the package that is to be opened. In addition, there is a need for flat trays that minimize the side of outer pouches and that minimize pouch buckling. Moreover, there remains a need for packages for top heavy medical device that enable medical personnel to consistently perform sterile transfers while minimizing the chance of dropping the medical devices.

SUMMARY OF THE INVENTION

There are a number of challenges associated with packaging medical devices that are relatively large, bulky and/or heavy, which require sterilization (e.g., EtO sterilization), and that are enclosed in sealed outer pouches, such as foil pouches. One challenge relates to holding the packaged device in place to avoid damage to the device and/or to the sealed outer pouch. Another challenge involves insuring that the outer pouch is not stressed during an EtO vacuum drying cycle and subsequent shipping and handling. An additional challenge involves removing a medical device from the package without the need to disassemble the package, e.g., remove the lid when the package has lateral constraints holding the device in place. Yet another challenge relates to providing packages for top heavy medical device that enable medical personnel to consistently perform sterile transfers while minimizing the chance of dropping a top heavy medical device. The above-mentioned problems are especially challenging when the package includes a thermoformed tray.

In one embodiment of the present invention, a package for a medical device desirably includes a tray having proximal and distal ends, top and bottom surfaces, lateral retention elements, and proximal and distal retention elements, and a proximal retainer sleeve fastened to a proximal section of the tray that covers the top surface of the tray. The retainer sleeve preferably has a section that can be rotationally displaced to expose a portion of a medical device disposed on the tray and to allow the medical device to be removed from the tray by rotating a proximal end of the medical device and, after the proximal end is clear of proximal retention elements, moving the medical device in a proximal direction to remove the device from the proximal end of the tray.

In one embodiment of the present invention, a method of dispensing a medical device from a medical device package preferably includes grasping the medical device located at the proximal end of the tray, rotating the medical device sufficiently to enable one side of the medical device to clear at least one retention element, and moving the medical device in a proximal direction away from the medical device package until the medical device is completely disengaged from the medical device package.

In one embodiment, a package for a medical device preferably includes a tray having a top surface, a bottom surface, a proximal end, a distal end, and first and second lateral sides that extend between the proximal and distal ends. The tray desirably has molded elements projecting from the top surface. The package preferably includes a retainer lid secured to the tray for covering the top surface of the tray at the distal end of the tray, and a retainer sleeve having a distal end and a proximal end. The distal end of the retainer sleeve is wrapped around the top and bottom surfaces of the tray and is secured to the tray by the retainer lid. The proximal end of the retainer sleeve includes a top panel that covers the top surface of the tray at the proximal end of the tray. The top panel of the retainer sleeve has a free edge that is adapted to flex away from the top surface of the tray to provide access to the medical device.

In one embodiment, the retainer sleeve includes a cut that extends between the free edge of the top panel and the distal end of the retainer sleeve for enabling the free edge of the top panel to move relative to the distal end of the retainer sleeve.

In one embodiment, the tray is made of a polymer material. In one embodiment, the tray is thermoformed and is made of high-density polyethylene (HDPE). In one embodiment, the molded elements of the tray preferably define a first channel adjacent the proximal end of the tray, a second channel distal to the first channel that extends toward the distal end of the tray, and at least one retaining element located at the proximal end of the tray. In one embodiment, the at least one retaining element includes a pair of retainer posts that are spaced from one another at the proximal end of the tray. When the medical device is loaded onto the tray, the retainer posts prevent proximal movement of the medical device relative to the tray.

In one embodiment, the molded elements on the tray desirably include a mound located between the first and second channels. The mound preferably has a top surface including a flat proximal section and a sloping distal section that slopes downwardly toward the distal end of the tray. The first and second channels desirably intersect one another at the mound. In one embodiment, the first and second channels define recesses molded into the tray and the mound projects above the recesses of the first and second channels. In one embodiment, the mound has a proximal face that opposes the first and second retainer posts. A handle of a medical device is disposed between the retainer posts and the proximal face of the mound, which prevents proximal and distal movement of the medical device relative to the tray.

In one embodiment, the top surface of the tray preferably includes a central depression that extends between the proximal edge of the tray and the proximal face of the mound. The central depression is desirably located between the first and second retainer posts.

In one embodiment, the medical device preferably has a handle and an elongated shaft extending from the handle. When the medical device is positioned on the tray, the handle is preferably disposed in the first channel of the tray and the elongated shaft is preferably disposed in the second channel of the tray. When secured to the tray, the top panel of the retainer sleeve preferably covers the handle of the medical device. The cut formed in the retainer sleeve desirably enables the free edge of the top panel to be flexed away from the handle and the top surface of the tray to allow access to and removal of the medical device from the tray.

In one embodiment, the top surface of the tray preferably has one or more snap-fit depressions molded therein at the distal end of the tray and the retainer lid has one or more snap-fit projections molded therein that extend from a bottom surface thereof. The one or more snap-fit projections of the retainer lid are preferably insertable into the one or more snap-fit depressions of the tray for securing the retainer lid to the tray.

In one embodiment, the distal end of the retainer sleeve desirably has one or more cutouts that are aligned with at least one of the one or more snap-fit depressions molded in the tray. In one embodiment, at least one of the one or more snap-fit projections on the retainer lid pass through the one or more cutouts and into a corresponding snap-fit depression for securing the distal end of the retainer sleeve to the tray.

In one embodiment, the retainer sleeve preferably includes a bottom panel that is adapted to cover the bottom surface of the tray, a top panel that is attached to a first edge of the bottom panel, and a connecting panel attached to a second edge of the bottom panel. The retainer sleeve is foldable for being wrapped around the tray for covering the top and bottom surfaces and the first and second lateral sides of the tray.

In one embodiment, the tray preferably includes a polymer material, such as high-density polyethylene (HDPE), the retainer lid desirably includes a polymer material, such as polypropylene (PP), and the retainer sleeve is preferably made of a cellulose material, such as paperboard. In one particular preferred embodiment, the tray is made of HDPE, the retainer lid is made of PP, and the retainer sleeve is paperboard.

In one embodiment, the tray thins toward the distal end of the tray so that the proximal end of the tray is thicker and the distal end of the tray is thinner.

In one embodiment, the package desirably includes an outer pouch that receives the package, such as a sealable foil pouch. The outer pouch is adapted to receive the assembled package including the tray, the medical device on the tray, the retainer lid and the retainer sleeve.

In one embodiment, the tray has a peripheral flange that extends around the outer perimeter of the tray. The flange may include segmented lifts projecting from an underside of the flange. The flange divides the tray into a topside and a bottom side so that the top surface of the tray is located above the peripheral flange and the bottom surface of the tray is located below the peripheral flange.

In one embodiment, a package for a medical device preferably includes a thermoformed tray having a top surface, a bottom surface, a proximal end, a distal end, and first and second lateral sides that extend between the proximal and distal ends. A medical device is disposed over the top surface of the tray, the medical device having a handle and an elongated shaft projecting from the handle. The tray preferably has molded elements projecting from the top surface including a first channel for receiving the handle, a second channel for receiving the elongated shaft, a mound located between the first and second channels, and a pair of retainer posts located at the proximal end of the tray. In one embodiment, the handle is disposed between the retainer posts and the mound for minimizing proximal and distal movement of the medical device relative to the tray.

In one embodiment, the package preferably includes a thermoformed retainer lid secured to the tray for covering the elongated shaft of the medical device at the distal end of the tray, and a retainer sleeve having a distal end and a proximal end, the distal end of the retainer sleeve being wrapped around the tray to cover the top and bottom surfaces of the tray. In one embodiment, the distal end of the retainer sleeve is secured to the tray by the retainer lid. In one embodiment, the proximal end of the retainer sleeve desirably includes a top panel that covers the top surface of the tray at the proximal end of the tray. The top panel of the retainer sleeve preferably has a free edge that is adapted to flex away from the top surface of the tray to provide access to the handle of the medical device. In one embodiment, the handle preferably has a base and the handle is pivotable about the base to clear the handle of the retainer posts so that the medical device is free to be moved in a proximal direction relative to the tray to remove the medical device from the tray.

In one embodiment, the tray is thermoformed and is desirably made from HDPE. In one embodiment, the tray is inclined so that it is thicker at the proximal end and thinner at the distal end of the device, which minimizes the pouch size while allowing for a smooth seal line to be formed on the foil pouch. In one embodiment, the thicker end of the tray is loaded into the pouch so that the thinner end of the tray is adjacent the final seal to be formed for completely sealing the pouch.

In one embodiment, the bottom surface of the tray preferably has one or more segmented lifts that offset the peripheral flange on the tray from the seal of the outer pouch to minimize the likelihood of the peripheral flange of the tray damaging or compromising the seal of the outer pouch. The segmented lifts also preferably facilitate the flow of sterilization gasses throughout the outer pouch and around the tray, and may also protect the outer pouch from being cut by the peripheral flange of the tray.

In one embodiment, the above-described retainer sleeve is replaced by a cover flap that does not wrap completely around the tray, that is attached to one lateral side of the tray, and that is secured to the tray by the retainer lid. In one embodiment, a package for a medical device desirably includes a tray having a top surface, a bottom surface, a proximal end, a distal end, and first and second lateral sides that extend between the proximal and distal ends. The tray preferably has elements, such as molded elements, projecting from the top surface of the tray for holding a medical device. The package desirably includes a retainer lid secured to the tray for covering the top surface of the tray at the distal end of the tray, and the cover flap having a distal end and a proximal end. In one embodiment, a lateral edge of the cover flap is attached to one lateral side of the tray and the distal end of the cover flap is secured to the tray by the retainer lid. The cover flap preferably covers the top surface of the tray at the proximal end of the tray. The cover flap desirably has a free edge that is adapted to flex away from the top surface of the tray for providing access to a medical device loaded on the tray.

In one embodiment, the tray is formed to accommodate an elongated medical device, such as a medical device having a straight or curved distal portion, e.g., a shaft.

In one embodiment, the multi-component package preferably includes a retainer lid that is secured over the top surface of the tray for covering a distal end of the tray. In one embodiment, the retainer lid may be snap-fit onto the tray.

In one embodiment, the distally located retainer lid is made from polypropylene (PP). Although the present invention is not limited by any particular theory of operation, it is believed that using HDPE for the tray and PP for the retainer lid allows for flexural rotations up to 30° without loss of snap-fit performance, which helps to keep the tray and the retainer lid together during shipping and handling. Moreover, both HDPE and PP are hydrophobic materials, which are preferred over other thermoform materials (e.g., PET) for an EtO sterilization process that needs to be vacuum dried before final sealing. Both HDPE and PP are preferred over other thermoform materials such as PET and PVC because the trimmed edges of HDPE and PP thermoform are comparatively not as sharp as other thermoform materials (e.g., PET and PVC).

In one embodiment, the PP retainer lid is preferably clear so as to provide a visual indication of the presence of the medical device in the tray. In one embodiment, the retainer sleeve is not made of paperboard but is made of a clear material such as a flexible, semi-rigid plastic film (e.g., PP). In one embodiment, the package may include a desiccant material that is separate from the retainer sleeve.

In one embodiment, the retainer lid desirably snap fits onto the tray. In one embodiment, the retainer lid has snap-fit projections that extend from the bottom surface of the retainer lid that are inserted into corresponding snap-fit depressions formed in the top surface of the tray. In one embodiment, when the retainer lid and the tray are secured together, a gap is provided between the snap-fit projections on the retainer lid and the corresponding snap-fit depressions on the tray, which facilitates efficient EtO gas infiltration throughout the top and bottom surfaces of the tray.

In one embodiment, the retainer lid is preferably transparent, which allows for visibility of the medical device within the assembled package.

In one embodiment, the multi-component package preferably includes a retainer sleeve that is secured to a proximal end of the tray. The retainer sleeve preferably provides a smoothing element that isolates the tray and the medical device from an outer pouch. In one embodiment, the retainer sleeve is made of paperboard and serves as a desiccant, which is particularly beneficial for EtO sterilized absorbable products.

In one embodiment, the paperboard retainer sleeve preferably includes a cut that enables a portion of the retainer sleeve to be flexed away from the top surface of the tray to expose a portion of the medical device, which enables medical personnel to access the medical device and remove the medical device from the package without requiring disassembly of the package. The paperboard sleeve is preferably secured to the tray and the retainer lid by means of a snap-fit connection between the retainer lid and the tray.

In one embodiment, the retainer sleeve that is secured to the tray by the retainer lid wraps completely around the tray (e.g., 360°). Thus, the retainer sleeve covers deep recesses formed in the underside of the tray, which is important during a vacuum drying cycle associated with an EtO sterilization process by keeping the pouch as smooth as possible on both the top surface and bottom surface of the tray. In addition, the wrap-around retainer sleeve provides enhanced security by preventing accidental dropping of the medical device while still allowing for an efficient method of dispensing the medical device from the package.

In one embodiment, the tray, the medical device on the tray, the retainer sleeve and the retainer lid are placed into an outer pouch that may be sealed. In one embodiment, the outer dimensions of the tray preferably closely match the seal line of the outer pouch. The close match between the outer perimeter of the tray and the inner seal line of the outer pouch limits movement of the tray relative to the outer pouch, which is especially important during shipping and handling.

The tray, the retainer lid, and the retainer sleeve desirably protect the outer pouch from being impacted by the medical device during loading, sterilization, shipping and handling of the package. The tray further protects the medical device by restraining the medical device from moving within the plane of the tray during shipping and handling of the package.

In one embodiment, the location of an integrated paperboard retainer sleeve allows for one-handed device dispensing. The cut on the paperboard retainer sleeve allows a top panel of the retainer sleeve to be easily flexed, which enables easy access and removal of a medical device from the tray. In one embodiment, when the medical device includes a handle, flexing the retainer sleeve away from the top surface of the tray allows a user to easily grip the handle and rotate the handle away from the top surface of the tray for removing the medical device from the tray. Although the retainer elements at the proximal end of the tray desirably block the medical device from shifting within the plane of the tray, the handle of the medical device may be rotated away from the retaining elements so that the handle is unconstrained by the retainer elements. Once the handle is rotated into a position whereby it is clear of the retainer elements, the handle may be pulled in a proximal direction to remove the medical device from the proximal end of the tray.

In one embodiment, after the medical device has been removed from the tray, the retainer lid and the paperboard retainer sleeve may be separated from one another so that the tray, the retainer lid and the retainer sleeve may be recycled.

These and other preferred embodiments of the present invention will be described in more detail below.

BRIEF DESCRIPTION OF THE DRAWING

FIG. 1 shows a package for a medical device including a tray, a retainer lid, a retainer sleeve, the medical device, and an outer pouch, in accordance with one embodiment of the present invention.

FIGS. 9A-9I show a method of securing a medical device in a package, in accordance with one embodiment of the present invention.

FIG. 11 shows a package for a medical device including a tray, a retainer lid, a retainer sleeve, the medical device, and an outer pouch, in accordance with one embodiment of the present invention.

FIGS. 16A-16G show a method of assembling a package containing a medical device, in accordance with one embodiment of the present invention.

FIG. 17A shows a package for a medical device including a tray, a medical device, a retainer lid, and a cover flap, in accordance with one embodiment of the present invention.

DETAILED DESCRIPTION

Figure 2A:
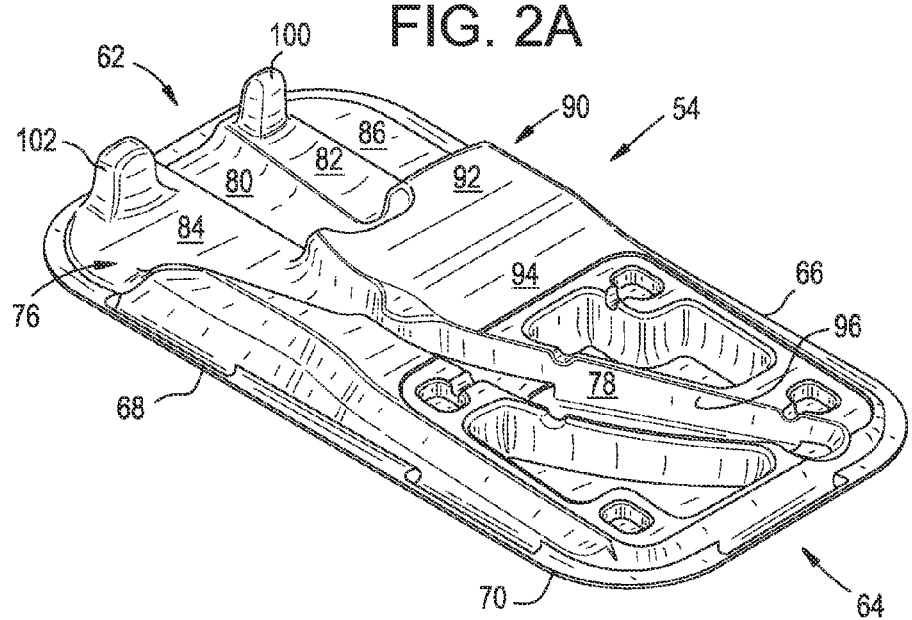
FIG. 2A shows a perspective view of the tray shown in FIG. 1.

Referring to FIG. 1, in one embodiment, a package 50 for a medical device 52 preferably includes a tray 54 adapted to receive the medical device 52, a retainer lid 56 that is snap-fit onto a distal end of the tray 54, and a retainer sleeve 58, that is wrapped around the proximal end of the tray 54. As will be described in more detail herein, after the medical device 52 has been loaded onto the tray 54, the retainer sleeve 58 is wrapped around the tray and is secured to the tray by the retainer lid 56. The assembled package 50 may be inserted into an open end of a sealable outer pouch 60, such as a foil pouch.

Figure 2B:
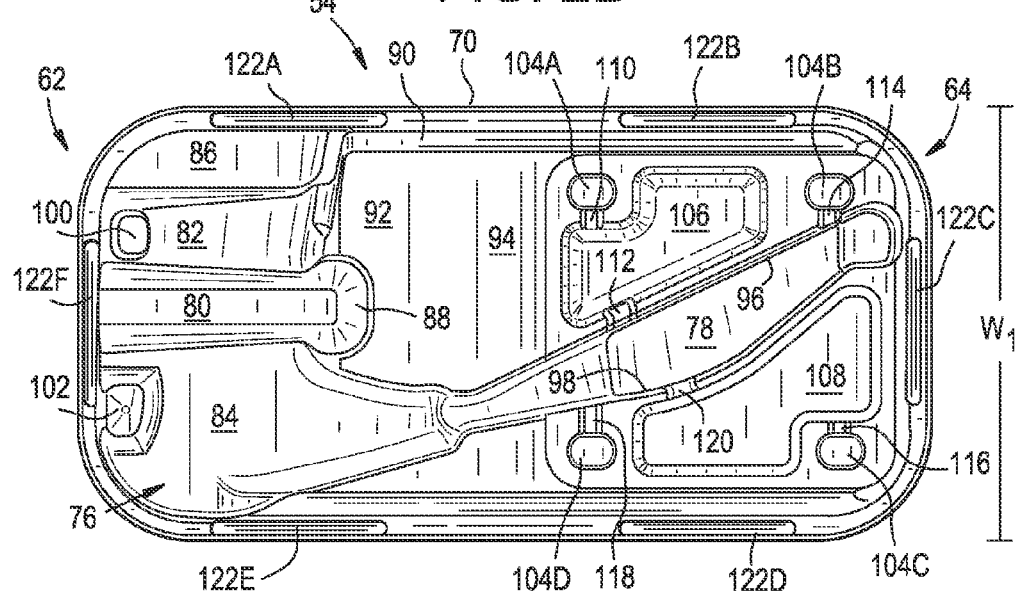
FIG. 2B shows a top plan view of the tray shown in FIG. 1.
Figure 2C:
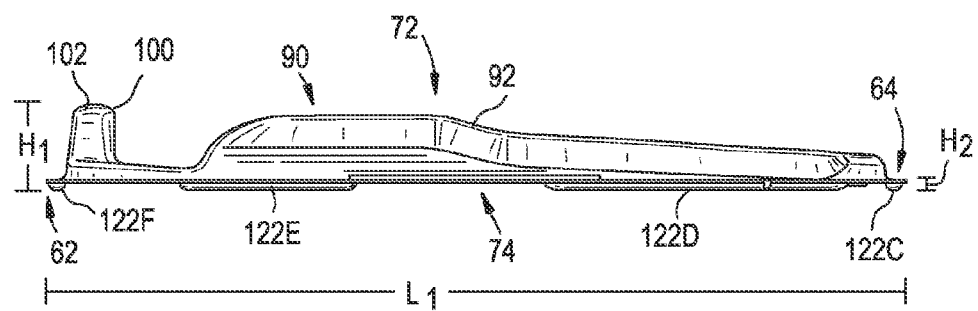
FIG. 2C shows a side elevation view of the tray shown in FIG. 1.

Referring to FIGS. 2A-2D, in one embodiment, the tray 54 of the package desirably includes a proximal end 62, a distal end 64, a first lateral side 66, and a second lateral side 68. The tray 54 preferably has a peripheral outer flange 70 that extends around the outer perimeter of the tray. Referring to FIG. 2C, the flange 70 preferably divides the tray 54 into a top surface 72 configured to receive a medical device, and a bottom surface 74 that is opposite the top surface 72. In one embodiment, the tray 54 is preferably thermoformed and is made of a polymer material such as high-density polyethylene (HDPE).

Referring to FIGS. 2A and 2B, in one embodiment, the tray 54 preferably includes a first channel 76 molded into the top surface that is adapted to receive a handle portion of the medical device 52 shown in FIG. 1 of the present application. The tray 54 also desirably includes a second channel 78 molded into the top surface that is adapted to receive the elongated shaft of the medical device 52 (FIG. 1). The first channel 76 desirably includes a centrally located depression 80 bounded on a first side by a first flat surface 82 and a second side by a second flat surface 84. Thus, in one embodiment, the top surface of the tray at the proximal end 62 thereof is generally open and is not surrounded by vertically extending constraints other than retainer posts as will be further disclosed herein. The first channel 76 also desirably includes a second depression 86 located between the first flat surface 82 and the flange 70 at the outer perimeter of the tray 54. The tray 54 preferably includes a concave-shaped recess 88 located at the distal end of the first channel 76, which is molded into a proximal face of a mound 90 of the tray 54.

In one embodiment, the mound 90 is located at the distal end of the first channel 76. In one embodiment, the mound 90 preferably includes a proximal flat section 92 and a distal sloping section 94 that slopes downwardly toward the distal end 64 of the tray 54. As shown in FIG. 2C, the distal sloping section 94 of the mound 90 slopes downwardly toward the distal end 64 and the bottom side 74 of the tray 54 so that the proximal end of the tray is thicker than the distal end of the tray.

Referring to FIGS. 2A and 2B, the tray 54 also desirably includes the second channel 72 that passes through the mound 90 toward the distal end 64 of the tray. The second channel 78 includes a first wall 96 and an opposing second wall 98. In one embodiment, the second channel 78 is designed to receive an elongated shaft of a medical device. In one embodiment, the second wall 98 of the second channel 78 has a concave shape that conforms to a curved shape of an elongated shaft of a medical device.

Referring to FIGS. 2A-2D, in one embodiment, the tray 54 desirably includes a pair of spaced retention posts 100, 102 that are located adjacent the proximal end 62 of the tray. The proximally located retention posts 100, 102 are desirably spaced from one another by the central depression 80 formed in the first channel 76 of the tray. As will be described in more detail herein, the retention posts 100, 102 prevent a medical device loaded onto the tray from sliding and/or moving in a proximal direction relative to the tray. In one embodiment, the medical device is constrained from moving toward the proximal end of the tray by the retention posts 100, 102, however, the medical device may be removed from the tray by rotating the handle of the medical device away from the top surface of the tray until the handle is clear of the retention posts 100, 102. Once the handle is clear of the retention posts, the medical device may be pulled in a proximal direction for removing the medical device from the tray.

Referring to FIG. 2B, in one embodiment, the distal end 64 of the tray 54 preferably includes four snap-fit depressions 104A-104D molded into the top surface of the tray that are adapted to receive similarly shaped projections formed on an underside of the retainer lid 56 (FIG. 1), as will be described in more detail herein. The tray 54 preferably includes a first circulation chamber 106 for circulating EtO gasses, which is located between the first and second snap-fit depressions 104A, 104B, the outer perimeter flange 70 extending along the first lateral side of the tray and the first wall 96 of the second channel 78. The top surface of the tray 54 also desirably includes a second EtO gas circulating chamber 108 that is located between the third and fourth snap-fit depressions 104C, 104D, the outer perimeter flange 70 extending along the second lateral side of the tray and the second wall 98 of the second channel 78.

The top side of the tray 54 desirably includes a number of EtO gas circulating grooves formed therein to ensure that the EtO gasses may easily circulate throughout the top surface of the tray. In one embodiment, the tray includes a first groove 110 that provides fluid communication between the first snap-fit depression 104A and the first circulation chamber 106, a second groove 112 that provides fluid communication between the first circulation chamber 106 and the second channel 78, and a third groove 114 that provides fluid communication between the second snap-fit depression 104B and the second channel 78. The top surface of the tray 54 also desirably includes a fourth groove 116 that provides fluid communication between the third snap-fit depression 104C and the second channel 78, a fifth groove 118 that provides fluid communication between the fourth snap-fit depression 104D and the second gas circulation channel 108 and a sixth groove 120 that provides fluid communication between the second gas circulation chamber 108 and the second channel 78. In one embodiment, during an EtO sterilization process, the EtO gasses preferably pass through the first channel 76, the second channel 78, the first and second gas circulation chambers 106, 108, and the four snap-fit depressions 104A, 104D via the above described grooves 110-120 molded into the top surface of the tray 54.

Referring to FIGS. 2B and 2C, in one embodiment, the tray 54 preferably has a length $L_1$ of about 12-16 inches and more preferably about 14.875 inches, and a width $W_1$ of about 6-8 inches and more preferably about 7.606 inches.

Figure 2D:
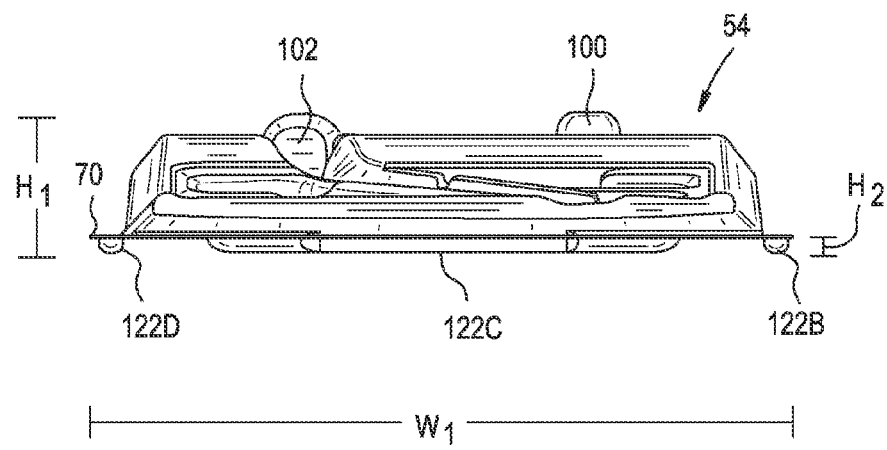
FIG. 2D shows a distal end elevation view of the tray shown in FIG. 1.

Referring to FIGS. 2B-2D, in one embodiment, the tray 54 preferably includes spacers 122A-122F projecting from the bottom surface of the peripheral flange 70. In one embodiment, first and second spacers 122A, 122B extend along the first lateral side 66 of the tray, a third spacer 122C extends along the distal end 64 of the tray, fourth and fifth spacers 122D, 122E extend along the second lateral side 68 of the tray, and a sixth spacer 122F extends along the proximal end 62 of the tray. As shown in FIGS. 2C and 2D, the spacers 122 preferably project from the bottom surface of the flange to lift the flange 70 away from an opposing inner surface of the outer pouch 60 (FIG. 1). Spacing the flange 70 away from the opposing inner surface of the pouch ensures efficient circulation of the EtO gasses around the tray 54 and also ensures that the outer flange 70 will not damage an opposing seal formed in the outer pouch 60.

Referring to FIGS. 2C and 2D, in one embodiment, the retention posts 100, 102 and the sixth spacer 122F at the proximal end 64 of the tray define a height $H_1$ of about 1-2 inches and more preferably about 1.490 inches. In one embodiment, the spacers 122 preferably define a height $H_2$ between the flange 70 and the lower end of the spacer of about 0.10-0.20 inches and more preferably about 0.156 inches.

Referring to FIG. 2C, in one embodiment, the tray 54 is preferably thicker at the proximal end 62 and thinner at the distal end 64. The tray 54 preferably narrows between the proximal end 62 and the distal end 64 of the tray so that the distal end 64 of the tray is thinner than the proximal end 62 of the tray.

Figure 3A:
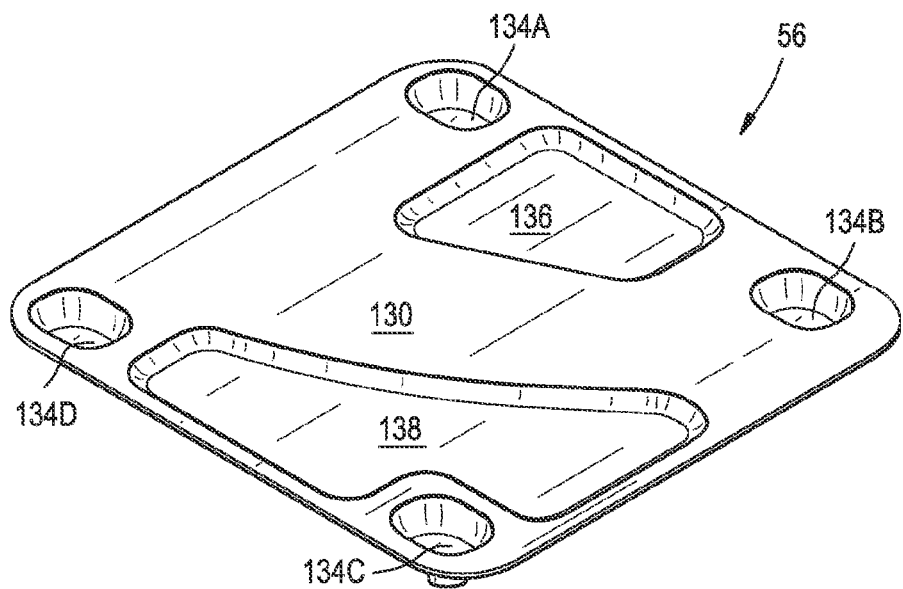
FIG. 3A shows a perspective view of the retainer lid shown in FIG. 1.
Figure 3B:
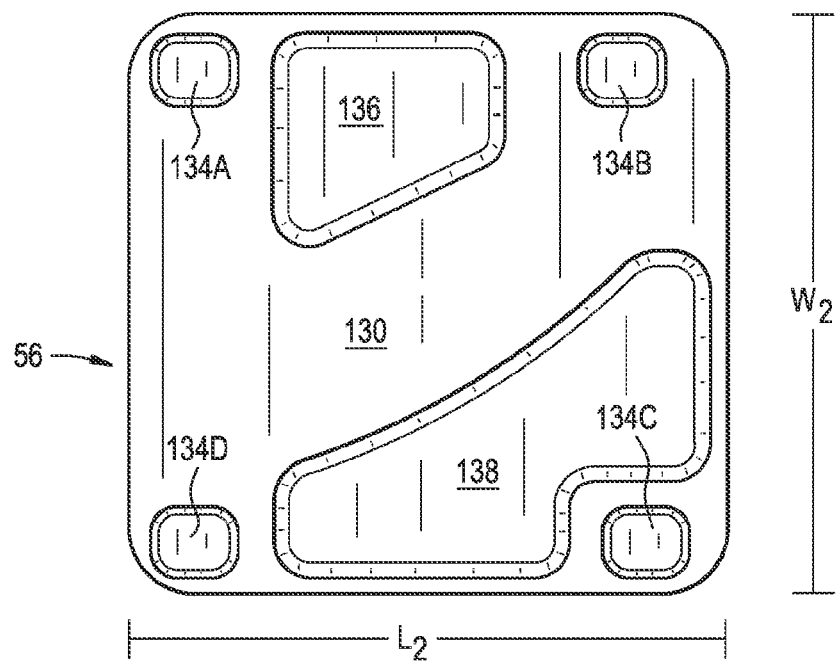
FIG. 3B shows a top plan view of the retainer lid shown in FIG. 1.
Figure 3C:
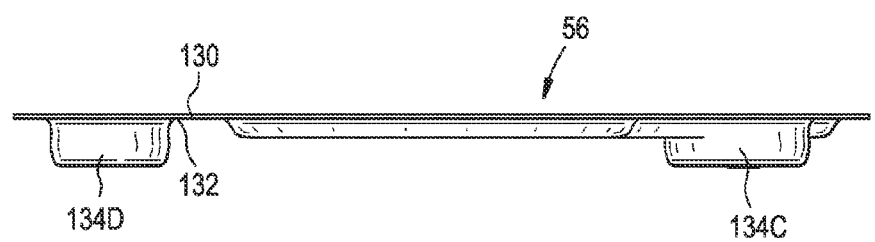
FIG. 3C shows a side elevation view of the retainer lid shown in FIG. 1.
Figure 3D:
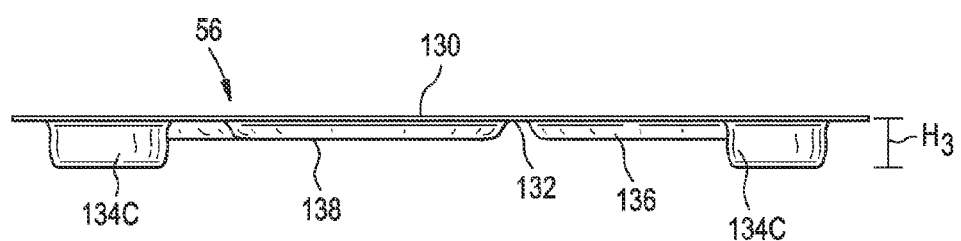
FIG. 3D shows a distal end elevation view of the retainer lid shown in FIG. 1.

Referring to FIGS. 3A-3D, in one embodiment, the retainer lid 56 preferably includes a top surface 130, a bottom surface 132, and four snap-fit projections 134A-134D that project from the bottom surface 132 thereof. The retainer lid 56 desirably includes a first depression 136 that conforms in size and shape to the first gas circulation chamber 106 in the tray 54 (FIG. 2B) and a second depression 138 sized and shaped to conform to the second gas circulation chamber 108 in the tray 54. As shown in FIG. 3D, the first and second depressions 136, 138 project from the bottom surface 132 of the retainer lid 56. As shown in FIG. 3D, each snap-fit projection 134A-134D defines a height $H_3$ of about 0.300-0.350 inches and more preferably about 0.320 inches.

Referring to FIG. 3B, in one embodiment, the retainer lid 56 has a length $L_2$ of about 5-7 inches and more preferably about 5.763 inches, and a width $W_2$ of about 5.5-6.5 inches and more preferably about 5.590 inches. As will be described in more detail below, the retainer lid 56 is desirably secured over the distal end of the tray 54 (FIGS. 2A-2D) for covering a distal end of a medical device (FIG. 1) loaded onto the tray. The retainer lid 56 also desirably secures the retainer sleeve to the tray.

Figure 4:
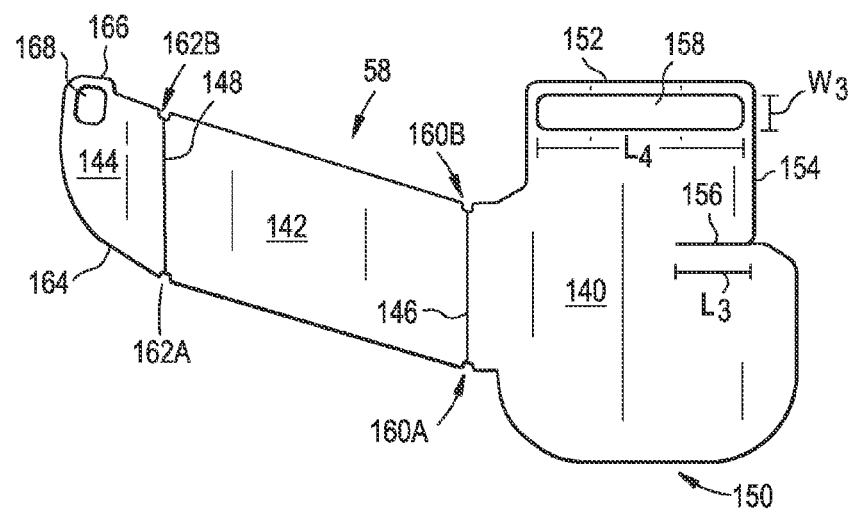
FIG. 4 shows a top plan view of the retainer sleeve shown in FIG. 1.

Referring to FIG. 4, in one embodiment, the retainer sleeve 58 preferably includes a paperboard blank having a top panel 140, a bottom panel 142 and a connecting panel 144. A first fold line 146 desirably extends between the top panel 140 and the bottom panel 142 for facilitating folding of the top panel over the bottom panel. The retainer sleeve 58 desirably includes a second fold line 148 that extends between the bottom panel 142 and the connecting panel 144 for facilitating folding of the bottom panel relative to the connecting panel.

In one embodiment, the top panel 140 desirably includes a proximal edge 150, a distal edge 152 and an outer edge 154. The top panel 140 desirably includes a cut 156 formed therein that extends from the outer edge 154 toward the first fold line 146. In one embodiment, the cut 156 has a length $L_3$ of about 1.50-1.75 inches and more preferably about 1.69 inches. In one embodiment, the top panel 140 includes an elongated cutout 158 that extends along the distal edge 152 thereof. In one embodiment, the elongated cutout 158 has a length $L_4$ of about 5.00-5.50 inches and more preferably about 5.22 inches and a width $W_3$ of about 0.50-1.00 inches and more preferably about 0.87 inches.

In one embodiment, a first pair of notches 160A, 160B may be provided at the ends of the first fold line 146 for facilitating folding of the top panel 140 and the bottom panel 142 relative to one another. The retainer sleeve 58 may also include a second pair of notches 162A, 162B provided at the ends of the second fold line 148 for facilitating folding of the bottom panel 142 and the connecting panel 144 relative to one another.

In one embodiment, the connecting panel 144 desirably includes a proximal edge 164 and a distal edge 166 with a second cutout 168 formed in the connecting panel adjacent the distal edge 166 thereof.

Figure 5A:
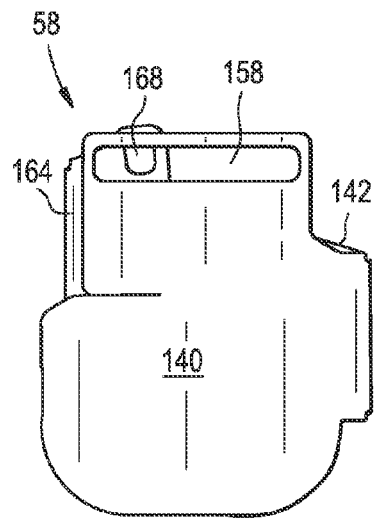
FIG. 5A shows a top view of the retainer sleeve of FIG. 4 after the retainer sleeve has been folded, in accordance with one embodiment of the present invention.
Figure 5B:
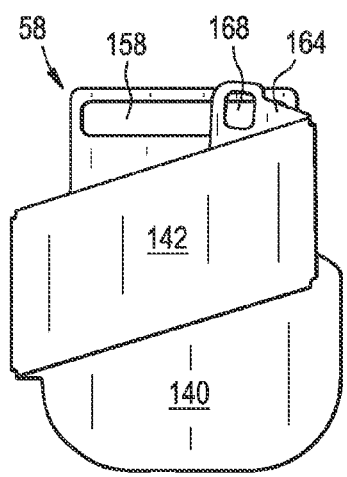
FIG. 5B shows a bottom view of the retainer sleeve of FIG. 4 after the retainer sleeve has been folded, in accordance with one embodiment of the present invention.

Referring to FIGS. 4 and 5A, in one embodiment, the retainer sleeve 58 is folded for being wrapped about the tray 54 shown and described above in FIGS. 2A-2D. In one embodiment, the connecting panel 164 is preferably folded over the bottom panel 142 and the top panel 140 is folded over the connecting panel 164. After the connecting panel has been folded over the bottom panel and the top panel has been folded over the connecting panel, the elongated cutout 158 at the distal end 152 of the top panel 140 is preferably aligned with the second cutout 168 at the distal end 166 of the connecting panel 164. As will be described in more detail herein, the first snap-fit projection 134A on the retainer lid (FIG. 3A) is passed through the aligned elongated cutout 158 and the second cutout 168 for at least partially securing the distal end of the retainer sleeve 58 to the tray 54 (FIG. 2A).

Figure 6:
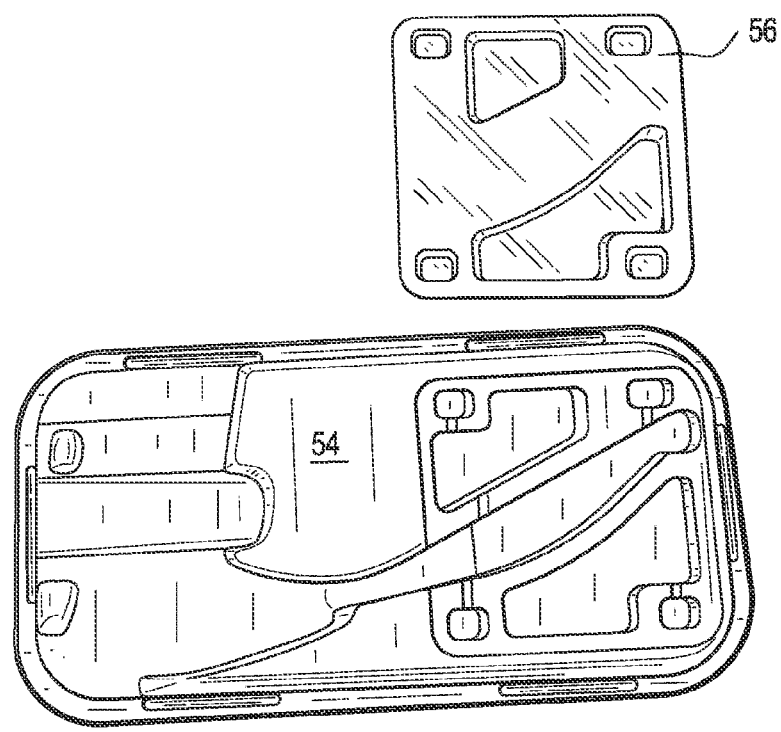
FIG. 6 shows a top plan view of the tray and the retainer lid of FIG. 1 before the retainer lid is secured over the distal end of the tray, in accordance with one embodiment of the present invention.

Referring to FIG. 6, in one embodiment, the tray 54 is configured to receive a medical device, such as an applicator instrument, by placing the tray atop a surface with the top surface of the tray facing away from the surface.

Figure 7A:
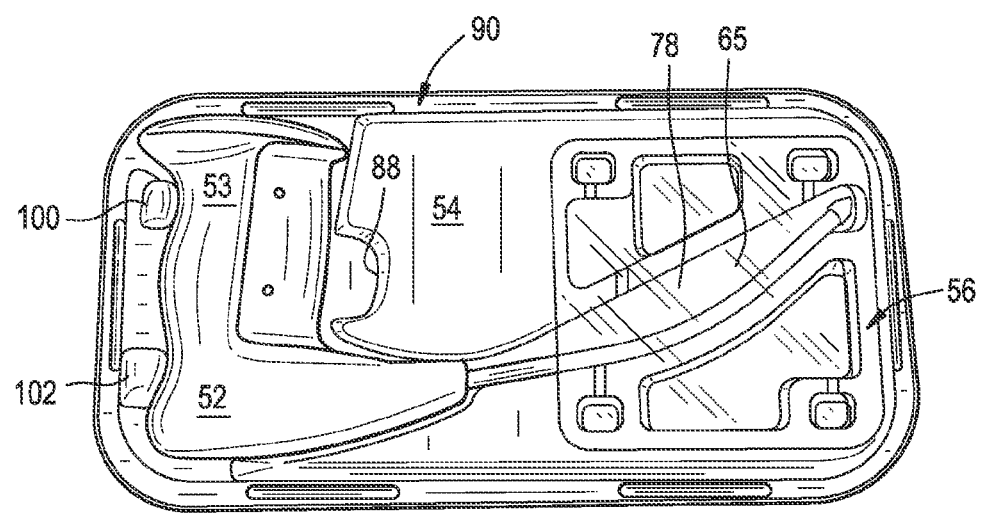
FIGS. 7A-7C show the medical device of FIG. 1 loaded onto the tray of FIG. 6 with the retainer lid secured over the distal end of the tray, in accordance with one embodiment of the present invention.

Referring to FIG. 7A, in one embodiment, a medical device 52 is placed onto the tray 54 with the handle 53 disposed in the first channel 76 and the curved elongated shaft 65 disposed in the second channel 78. When positioned on the tray, the leading face of the handle 53 opposes the concave shaped cutout 88 formed at the proximal end of the mound 90 and the trailing end of the handle 53 abuts against the first and second retaining posts 100, 102. As a result, the handle 53 is constrained from proximal and distal movement relative to the plane of the tray. The retainer lid 56 may be secured over the distal end of the tray 54 by inserting the four snap-fit projections on the retainer lid 56 into the four snap-fit depressions on the tray 54. In FIG. 7A, the retainer sleeve is not shown so that the position of the medical device 52 and the retainer lid 56 may be clearly displayed.

Figure 7B:
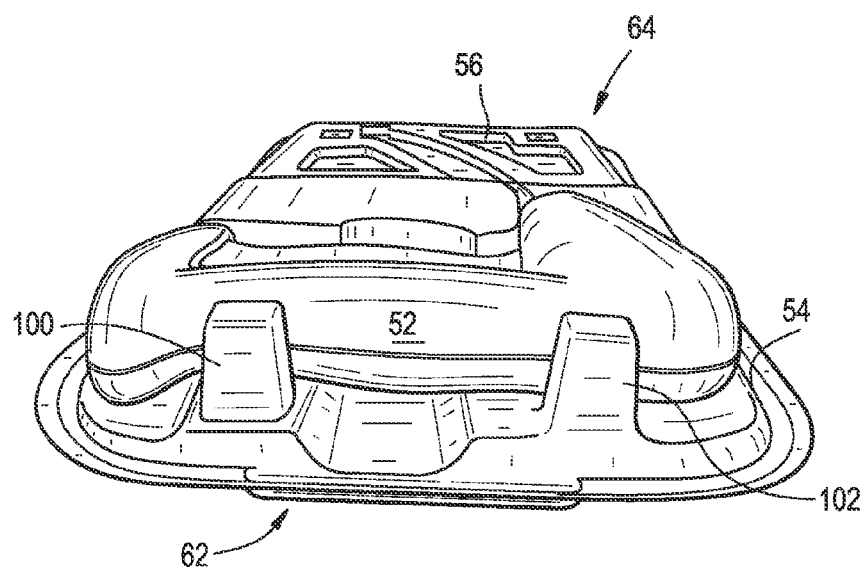

Referring to FIG. 7B, the first and second retaining posts 100, 102 act as stops that prevent proximal movement of the handle 53 of the medical device 52 toward the proximal end 62 of the tray 54. The retainer lid 56 is snap-fit onto the distal end 64 of the tray 54 for covering the elongated shaft of the medical device 52.

Figure 7C:
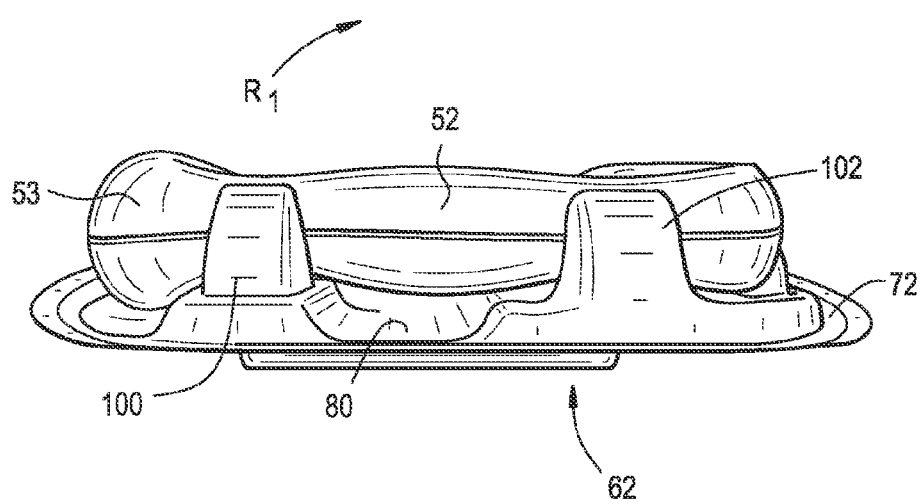

Referring to FIG. 7C, in one embodiment, the central depression 80 formed in the top surface 72 of the tray 54 extends between the first and second retaining posts 100, 102. In one embodiment, medical personnel may place a thumb into the central depression 80 and one or more fingers into the concave cutout 88 (FIG. 7A) for grasping the handle 53 of the applicator instrument 52 and rotating the handle 53 in the direction indicated by $R_1$. As will be described in more detail herein, the handle 53 is preferably rotated until it clears the retaining posts 100, 102 so that it may be slid proximally toward the proximal end 62 of the tray 54 (FIG. 7A) for removing the medical device 52 from the tray.

Figure 8:
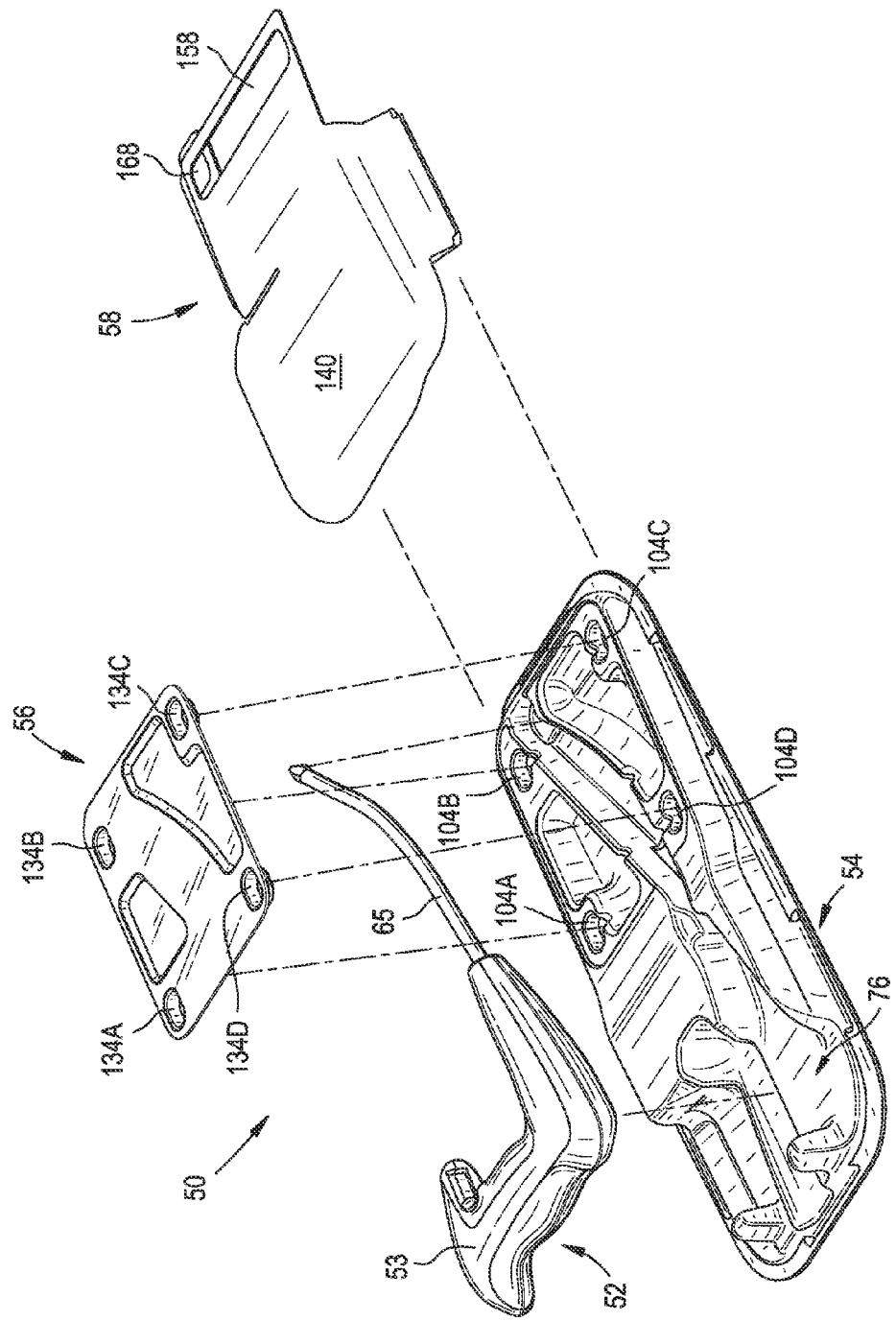
FIG. 8 shows a perspective view of the tray, the retainer lid, the retainer sleeve, and the medical device of FIG. 1 prior to assembly of the elements into a package, in accordance with one embodiment of the present invention.

FIG. 8 shows an exploded view of the components of a package 50 for a medical device 52 prior to assembly. The package 50 preferably includes the tray 54 adapted to receive the medical device 52 so that the handle 53 is disposed within the first channel 76 of the tray and the elongated shaft 65 is disposed within the second channel 78 of the tray. The retainer sleeve 58 is preferably wrapped about the proximal end of the tray 54 so that the top panel 140 of the retainer sleeve overlies the top surface 72 of the tray 54 with the elongated cutout 158 of the sleeve aligned with the snap-fit depressions 104A, 104C and the second cutout 168 aligned with the first snap-fit depression 104A. After the retainer sleeve 58 has been wrapped around the tray, the snap-fit projections 134A on the retainer lid 56 are inserted into the corresponding snap-fit depressions 104-104D on the tray 54 for securing the retainer lid 56 over the distal end of the tray 54. When the retainer lid 56 has been secured onto the tray 54, the first snap-fit projection 134A preferably passes through the second cutout 168 and the elongated first cutout 158 of the retainer sleeve 58 and is inserted into the first snap-fit depression 104A, and the fourth snap-fit projection 134D preferably passes through the elongated cutout 158 of the retainer sleeve 58 and is inserted into the fourth snap-fit depression 104D. Thus, the retainer lid 56 both covers the shaft 65 of the medical device 52 that is disposed in the second chamber 78 of the tray, and secures the distal end of the retainer sleeve 58 to the tray.

Referring to FIG. 9A, in one embodiment, the multi-component package 50 is assembled by placing the medical device 52 on the top surface of the tray 54 so that the handle portion 53 is disposed within the first channel 76 and the elongated shaft 65 is disposed within the second channel 78.

The bottom surface of the tray 54 is preferably positioned atop the retainer sleeve 58 with the tray aligned over the bottom panel 142 of the retainer sleeve. The first lateral side 66 of the tray 54 is preferably aligned with the first fold line 146 that extends between the bottom panel 142 and the connecting panel 144. The second lateral side 68 of the tray 54 is preferably aligned with the second fold line 148 extending between the bottom panel 142 and the top panel 140.

Referring to FIG. 9B, in one embodiment, the connecting panel 144 of the retainer sleeve 58 is folded over the first lateral edge 66 of the tray 54 so that its free end overlies the top surface of the tray 54. The first cutout 168 formed in the connecting panel 144 is preferably aligned with the first snap-fit depression 104A formed in the top surface of the tray 54. After the connecting panel 144 is folded over the top surface of the tray 54, the top panel 140 of the retainer sleeve 58 is desirably folded over the second lateral edge 68 of the tray 54 so that it overlies the top surface of the tray. After the top panel 140 has been folded over the top surface of the tray 54, the elongated cutout 158 of the top panel 140 is preferably aligned with the first snap-fit depression 104A and the fourth snap-fit depression 104D provided in the top surface of the tray.

Referring to FIG. 9C, in one embodiment, the retainer lid 56 is secured to the distal end 64 of the tray 54 via the snap-fit projections and snap-fit depressions. In one embodiment, the four snap-fit projections 138A-138D projecting from the bottom surface of the retainer lid 56 are inserted into the four snap-fit depressions 104A-104D formed in the top surface of the tray 54. The first snap-fit projection 134A on the retainer lid 56 desirably passes through the elongated cutout 158 on the top panel 140 and the second cutout 168 on the connecting panel 164 for attaching the retainer sleeve 58 to the tray 54. In addition, the fourth snap-fit projection 134D on the retainer lid 56 passes through the elongated slot 158 on the top panel 140 and into the fourth snap-fit depression on the tray 54 for attaching the retainer sleeve 58 to the tray.

In one embodiment, the retainer lid 56 may be split into two smaller retainer lids instead of one larger retainer lid to minimize material costs. The two smaller retainer lids desirably perform the same functions as the single retainer lid 56 shown and described herein. In one embodiment, the distal end of the retainer lid may be secured to the distal end of the tray via a hinge element. In one embodiment, the connected retainer lid may be pivoted about the hinge element from a first position to a second position for opposing and covering the top surface of the tray at the distal end of the tray.

After the retainer sleeve 58 has been secured to the tray 54 by the retainer lid 56, the top panel 140 desirably overlies the top surface of the tray at the proximal end 62 of the tray with the proximal edge 150 of the top panel 140 being substantially aligned with the proximal end 62 of the tray 54.

Figure 9E:
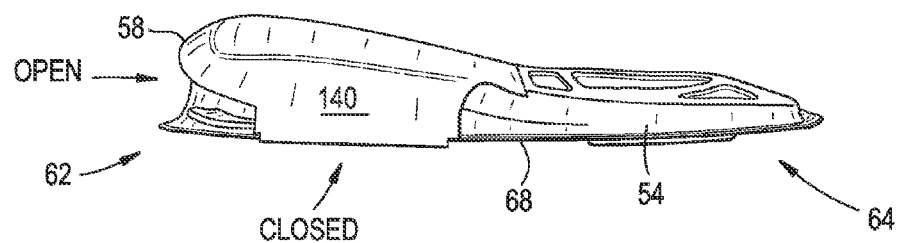

Referring to FIG. 9D, in one embodiment, after the retainer sleeve 58 has been secured to the tray 54, the bottom panel 142 desirably extends over the bottom surface 74 of the tray. Referring to FIG. 9E, the top panel 140 of the retainer sleeve 58 overlies the top surface of the tray 54. The top panel 140 desirably conforms to the sloping top surface of the tray 152 and slopes downwardly between the proximal end 62 and distal end 64 of the tray.

Figure 9F:
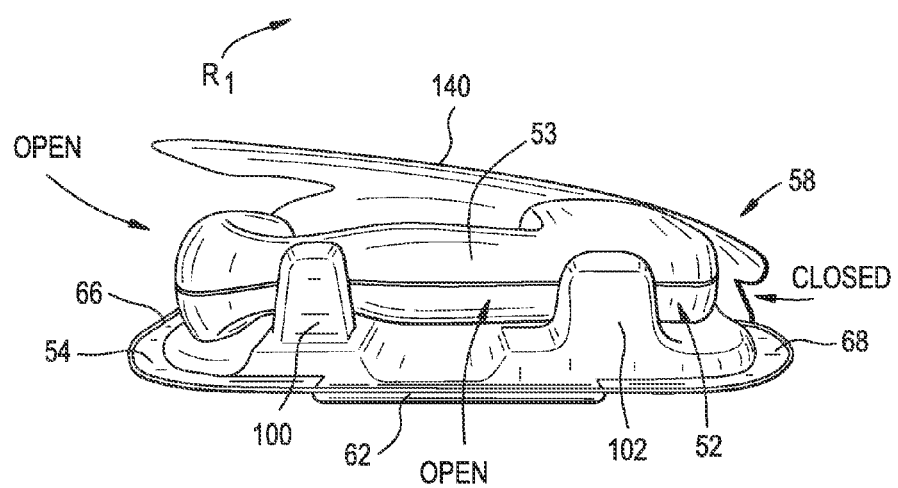

Referring to FIG. 9F, in one embodiment, the handle 55 of the medical device 52 lies adjacent the first and second retaining posts 101, 102 for preventing the medical device 52 from sliding in a proximal direction toward the proximal end 62 of the tray 54. The retainer sleeve 58 is wrapped around the proximal end 62 of the tray 54 with the top panel 140 overlying the handle 53 of the medical device 52 and the top surface of the tray 54. The cutout 156 formed the top panel 140 of the retainer sleeve 58 desirably enables the top panel 140 to be flexed away from the top surface of the tray in the direction indicated $R_1$.

Referring to FIGS. 9E and 9F, in one embodiment, the retainer sleeve 58 is "closed" along the second lateral side 68 of the tray 54, and is "open" along the proximal end 62 and the first lateral side 66 of the tray 54. The "closed" portion of the retainer sleeve 58 prevents the medical device 52 from being removed via the second lateral side 68 of the tray, however, the "open" portions of the retainer sleeve 58 enable the top panel 140 to be flexed away from the top surface 72 of the tray 54 so that the medical device may be pivoted away from the tray (see FIG. 9F for movement designated $R_1$), whereby the handle 53 clears the retainer posts 100, 102. Once the handle clears the retainer posts, the handle 53 may be pulled proximally through the "opening" at the proximal end of the retainer sleeve 58 at the proximal end 62 of the tray 54.

Referring to FIGS. 9G and 9H, in one embodiment, the assembled package 50 containing the medical device 52 is inserted through an open end of a sealable outer pouch 60. Initially, when loading the tray into the outer pouch 60, the outer pouch is preferably sealed along a first lateral edge 170, a proximal edge 172 and a second lateral edge 174. The distal edge 176 is open for receiving the package. In one embodiment, the proximal end 62 of the tray 54 is inserted into the open end 176 of the pouch 60 in the direction indicated $A_1$. Thus, the thicker proximal section 62 of the tray 54 is the first end of the tray to be inserted into the pouch and is trailed by the thinner, distal end 64 of the tray.

In one embodiment, the outer pouch is preferably a sealable foil pouch including first and second foil sheets that are joined together as disclosed in commonly assigned U.S. Pat. No. 8,292,076 to Dacey, the disclosure of which is hereby incorporated by reference herein.

Figure 9I:
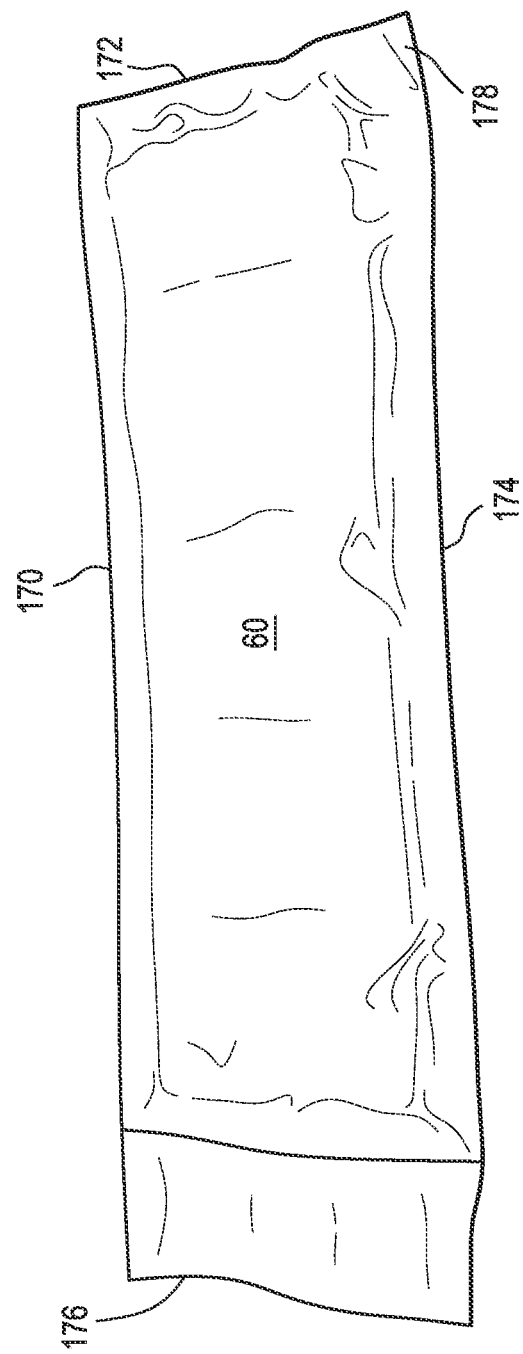

FIG. 9H shows the package 50 after it has been further inserted into the outer pouch 60. FIG. 9I shows the outer pouch 60 after the package 50 has been fully inserted therein. In one embodiment, EtO gasses are circulated throughout the interior of the pouch 60 and around the medical device and the tray and, after vacuum drying, the open end 176 of the outer pouch is sealed for completely sealing the outer pouch. In one embodiment, the outer pouch 60 includes an opening tab 178 that is provided in a corner of the pouch located between the proximal edge 172 and the second lateral edge 174. Referring to FIGS. 9E, 9F, and 9I, the openings in the retainer sleeve 58 located along the first lateral side 66 and the proximal end 62 of the tray 54 are preferably disposed adjacent the opening tab 178 of the outer pouch 60 to provide for easy access to the handle of the medical device when the opening tab 178 is peeled open.

In one embodiment, the assembled package including the medical device and the outer pouch are subjected to a sterilization process to sterilize the medical device and the components of the package. One preferred sterilization process may involve a gas diffusion sterilization method. In one embodiment, the sterilization method preferably involves using ethylene oxide (EtO) gasses. Ethylene oxide is commonly used in the healthcare industry for sterilizing medical devices because of its non-damaging effects on delicate instruments and devices that must be sterile, and for its compatibility with a wide range of packaging materials. EtO methods are frequently used for medical devices having parts that cannot tolerate heat, moisture or abrasive chemicals, such paper, rubber and plastic parts. Using EtO gasses for the sterilization of medical devices was initially developed by the U.S. military and remains the most commonly used in many industries.

In one embodiment, after EtO sterilization gasses has been circulated throughout the interior of the pouch 60 and around the package disposed inside the pouch, the open end 176 of the pouch 60 is sealed so that the package is fully sealed within the outer pouch 60.

Figure 10A:
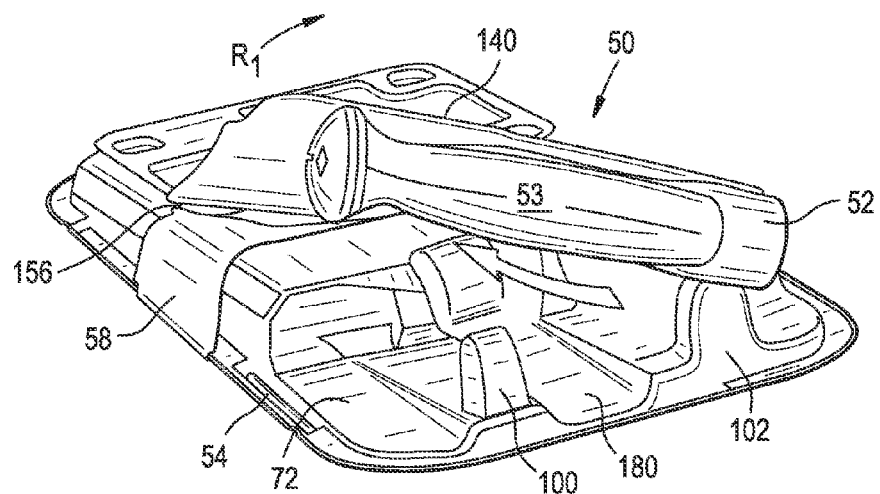
FIGS. 10A-10B show a method of removing a medical device from a package, in accordance with one embodiment of the present invention.

Referring to FIG. 10A, in one embodiment, after the tab 178 (FIG. 9I) on the outer pouch 60 has been peeled apart and/or broken, surgical personnel may reach into the opened pouch 60 to access the medical device 52 disposed on the tray 54. In one embodiment, a surgeon places his or her hand between the top panel 140 of the retainer sleeve 58 and the central depression 180 located between the first and second retainer posts 100, 102 to grasp the handle 53 of the medical device 52 with the thumb, fingers and palm of the hand. The handle 53 is preferably pivoted about its base in the direction $R_1$ so that the handle 53 is clear of the first and second retaining elements 100, 102. As the handle 53 of the medical device 52 is pivoted in the direction $R_1$, the cut 156 formed in the top panel 140 enables the top panel 140 to flex away from the top surface 72 of the tray 54. As the top panel 140 flexes away from the top surface, the retainer lid 56 secures the distal end 152 of the retainer sleeve 58 to the top surface of the tray.

Figure 10B:
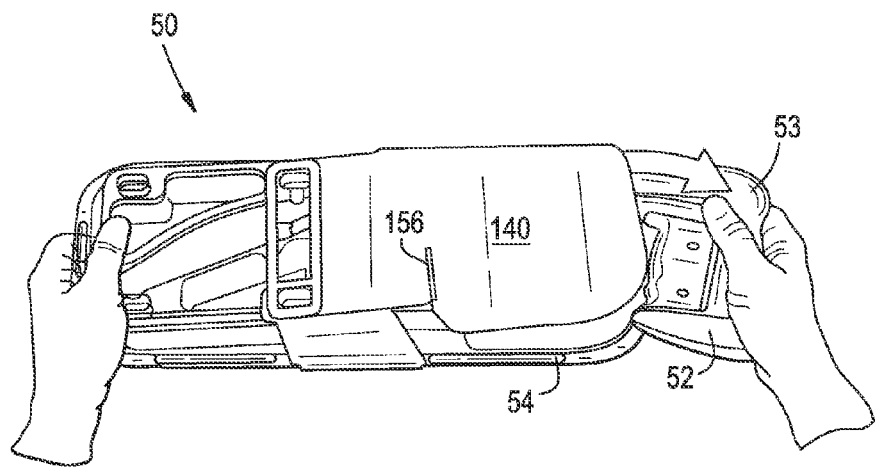

Referring to FIGS. 10A and 10B, once the handle 53 of the medical device 52 has been pivoted to the position shown in FIG. 10A, whereby the handle 53 is clear of the retainer posts 100, 102, the medical device 52 may be pulled in a proximal direction relative to the tray 54 for removing the medical device 52 from the tray.

Referring to FIG. 11, in one embodiment, a package 250 for a medical device 252 preferably includes a tray 254 adapted to receive the medical device 252, and a retainer lid 256 that is adapted to be secured to the tray 254, such as being snap-fit onto a distal end of the tray 254. The package desirably includes a retainer sleeve 258 that is wrapped around a proximal end of the tray 254 and is secured to the tray via the retainer lid 256. After the package 250 is assembled together, the assembled package may be inserted into an open end of a sealable, outer pouch 260 for being sterilized and sealed (e.g., air-tight sealed) within the outer pouch.

Figure 12A:
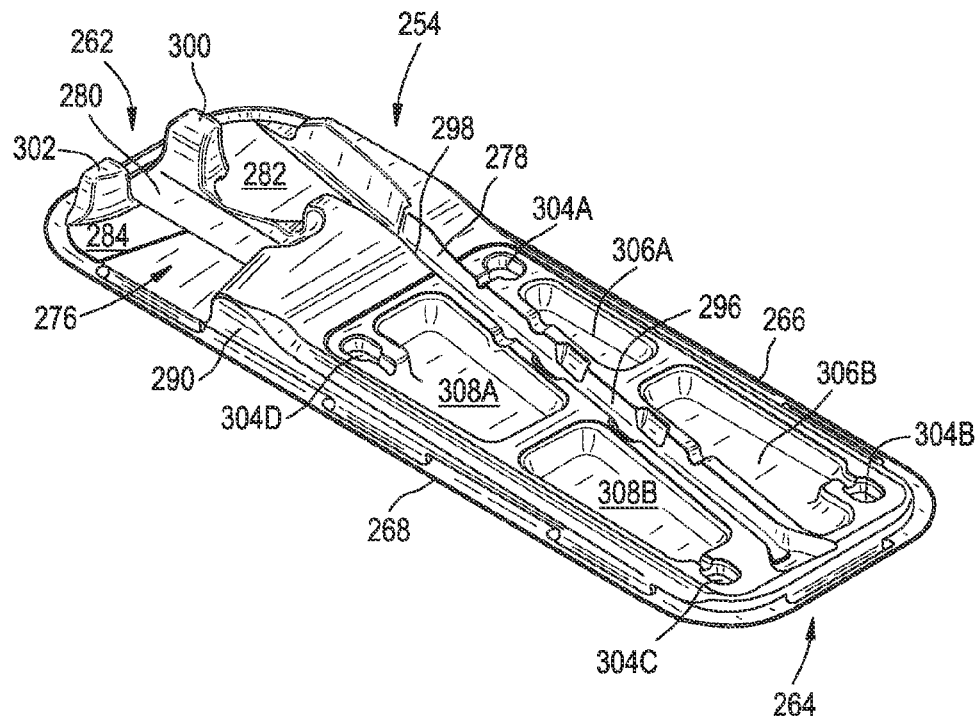
FIG. 12A shows a perspective view of the tray shown in FIG. 11.
Figure 12B:
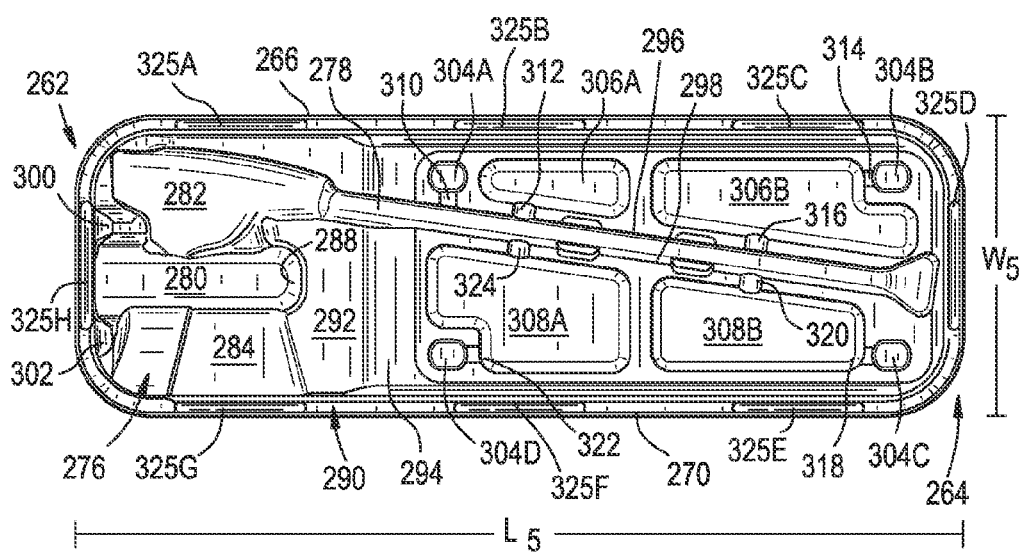
FIG. 12B shows a top plan view of the tray shown in FIG. 11.
Figure 12C:
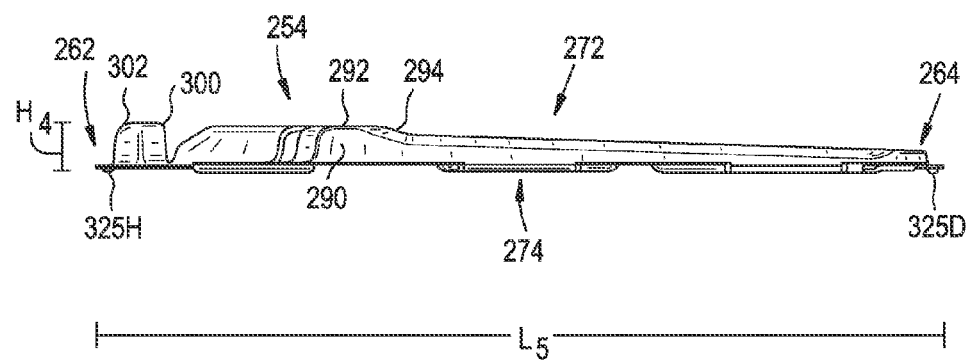
FIG. 12C shows a side elevation view of the tray shown in FIG. 11.

Referring to FIGS. 12A-12D, in one embodiment, the tray 254 desirably includes a proximal end 262, a distal end 264, a first lateral side 266, and a second lateral side 268. The tray 254 preferably has a flange 270 that extends around the outer perimeter of the tray. Referring to FIG. 12C, the flange 270 preferably divides the tray 254 between a top surface 272 configured to receive a medical device, and a bottom surface 274 that is opposite the top surface 272.

Referring to FIGS. 12A and 12B, in one embodiment, the tray 254 is preferably a thermoformed tray that includes a first channel 276 defining a depression molded in the top surface of the tray that is adapted to receive a handle of the medical device 252 (FIG. 11). The tray 254 also desirably includes an elongated second channel 278 molded therein that is adapted to receive the elongated shaft of the medical device 252 (FIG. 11). The first channel 276 desirably includes a centrally located depression 280 bounded on one side by a first flat surface 282 and a second side by a second flat surface 284. The distal end of the central depression 280 desirably includes a concave-shaped cutout 288 formed in a mound 290 of the tray 254 that is located between the first channel 276 and the second channel 278.

Referring to FIGS. 12A-12C, in one embodiment, the mound 290 preferably includes a proximal flat section 292 and a distal sloping section 294 that slopes downwardly toward the bottom surface 274 of the tray 254. As shown in FIG. 12C, the distal sloping section 294 of the mound 290 slopes downwardly toward the distal end 264 and the bottom surface 274 of the tray 254. Referring to FIG. 12C, in one embodiment, the proximal end 262 of the tray is thicker than the distal end 264 of the tray 254.

Referring to FIG. 12B, in one embodiment, the second channel 278 desirably includes a first wall 296 and an opposing second wall 298. In one embodiment, the first and second walls 296, 298 are generally straight and conform to the shape of the elongated shaft of the medical device 252 (FIG. 11).

Referring to FIGS. 12A-12D, in one embodiment, the tray 254 desirably includes a pair of spaced retention posts 300, 302 that are located adjacent the proximal end 262 of the tray. The proximally located retention posts 300, 302 are desirably spaced from one another by the central depression 280 formed in the top surface of the tray. As will be described in more detail herein, the retention posts 300, 302 retain the medical device on the tray 254 and prevent the medical device from sliding and/or moving (e.g., proximally) relative to the tray. In one embodiment, the medical device will not fall out of the tray 254 and will be retained inside the tray by the retention posts 300, 302 and the proximal face of the mound 290. The medical device may be removed from the tray by rotating the handle away from the top surface of the tray until the handle is clear of the retention posts 300, 302. Once the handle is clear of the retention posts 300, 302, the medical device may be pulled toward the proximal end 262 of the tray 254 for removing the medical device from the tray.

Referring to FIGS. 12A and 12B, in one embodiment, the distal end 264 of the tray 254 desirably includes four snap-fit depression 304A-304D that are adapted to receive similarly shaped snap-fit projections extending from an underside of the retainer lid 256 (FIG. 11), as will be described in more detail herein. The tray 254 preferably includes a first pair of EtO gas circulation chambers 306A, 306B for circulating EtO gasses that are located between the first and second snap-fit depressions 304A, 304B, the outer perimeter flange 270 extending along the first lateral side 266 of the tray, and the first wall 296 of the second channel 278. The top surface of the tray 254 also desirably includes a second pair of EtO gas circulating chambers 308A, 308B that are located between the third and fourth snap-fit depressions 304C, 304D, the outer perimeter flange 270 extending along the second lateral side 268 of the flange, and the second wall 298 of the second channel 278.

Referring to FIG. 12B, in one embodiment, the top surface of the tray 254 desirably includes a number of EtO gas circulating grooves formed therein to ensure that the EtO gasses may easily circulate throughout the tray. In one embodiment, the tray includes a first groove 310 that provides fluid communication between the first snap-fit depression 304A and the chamber 306A, a second groove 312 that provides fluid communication between the chamber 306A and the second channel 278, and a third groove 314 that provides fluid communication between the second snap-fit depression 104B and the chamber 306B. The top surface of the tray 254 also desirably includes a fourth groove 316 that provides fluid communication between the chamber 306B and the second channel 278, a fifth groove 318 that provides fluid communication between the third snap-fit depression 304C and the chamber 308B, and a sixth groove 320 that provides fluid communication between the chamber 308B and the second channel 278. In addition, the tray 254 preferably includes a seventh groove 322 that provides fluid communication between the fourth snap-fit depression 304D and the chamber 308A, and an eighth groove 324 that provides fluid communication between the chamber 308A and the second channel 278. In one embodiment, during an EtO sterilization process, the EtO gasses preferably pass over the top and bottom surfaces of the tray and through the first channel 276 and second channel 278. The EtO gasses also preferably pass through the grooves 310-324 and into the chambers 306A, 306B, 308A, and 308B and the four snap-fit depressions 304A-304D for circulating the sterilization gasses throughout the tray 254.

Referring to FIGS. 12B and 12C, in one embodiment, the tray 254 has a length $L_5$ of about 12-16 inches and more preferably about 14.875 inches, and a width $W_5$ of about 6-8 inches and more preferably 7.606 inches.

Figure 12D:
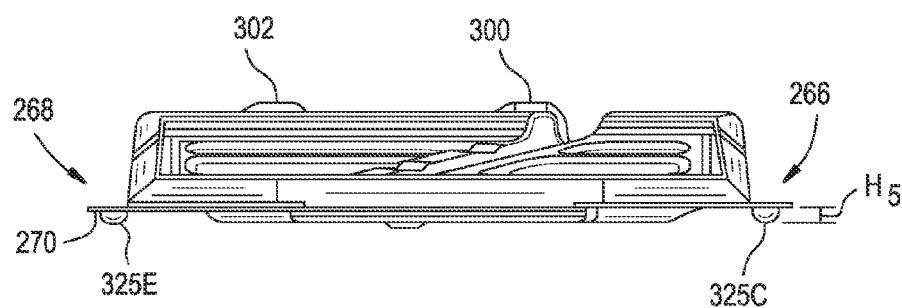
FIG. 12D shows a distal end elevation view of the tray shown in FIG. 11.

Referring to FIGS. 12A-12D, in one embodiment, the tray 254 preferably includes spacers 322A-322F projecting from the bottom of the peripheral flange 270. In one embodiment, three spacers 325A-325C extend along the first lateral side 266 of the tray, a single spacer 325D extends along the distal end 264 of the tray, three spacers 325F-325G extend along a second lateral side 268 of the tray, and a single spacer 325H extends along a proximal end 262 of the tray. Other embodiments may have more or fewer spacers on the flange. As shown in FIGS. 12C and 12D, the spacers 325 preferably project from the bottom surface 274 of the flange 270 to space the flange 270 away from an opposing inner surface of the outer pouch 260 (FIG. 11). Spacing the flange 270 away from the opposing inner surface of the pouch ensures thorough and efficient circulation of the EtO gasses and also ensures that the outer flange 270 will not damage (e.g., cut) an opposing seal formed inside the outer pouch 260.

Referring to FIG. 12C, in one embodiment, the retention posts 300, 302 and the eighth spacer 325H define a height $H_4$ of about 1-2 inches and more preferably about 1.490 inches. In one embodiment, the tray 254 preferably narrows and becomes thinner between the proximal end 262 and the distal end 264. In other words, the tray 254 tapers inwardly between the proximal end 262 and the distal end 264 so that the distal end 264 of the tray is thinner than the proximal end 262 of the tray.

Referring to FIG. 12D, in one embodiment, the spacers 325 preferably define a height $H_5$ between the flange 270 and the lower end of the spacer of about 0.10-0.20 inches and more preferably about 0.156 inches.

Figure 13A:
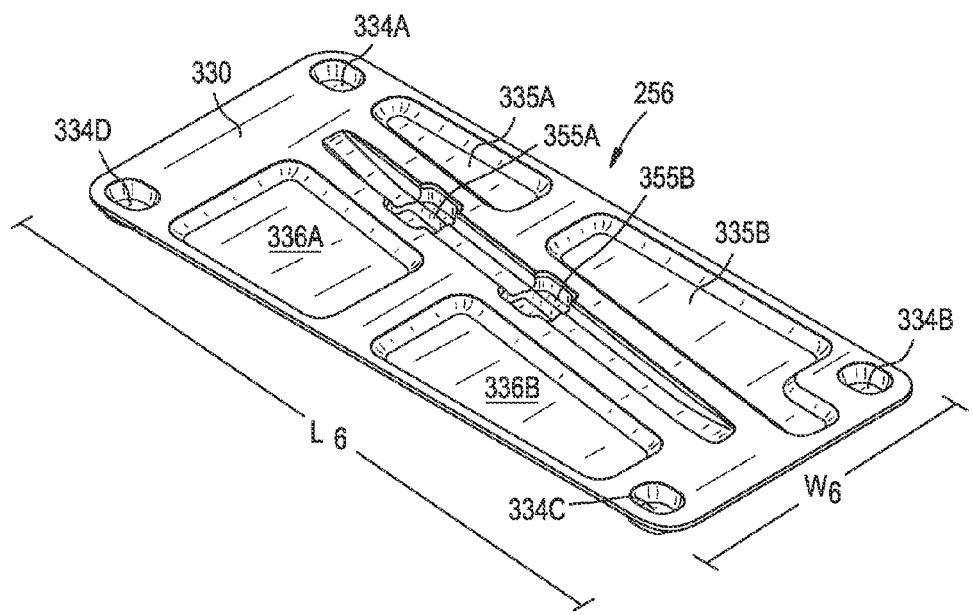
FIG. 13A shows a perspective view of the retainer lid shown in FIG. 11.
Figure 13B:
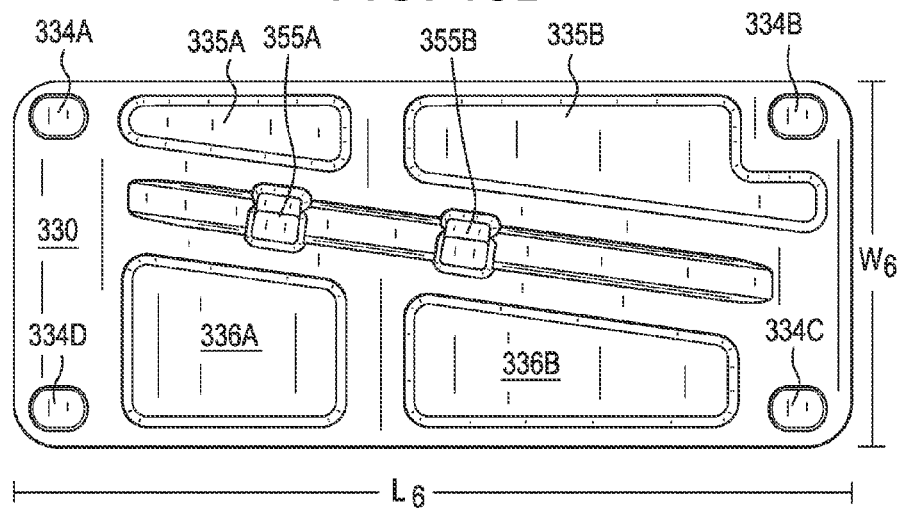
FIG. 13B shows a top plan view of the retainer lid shown in FIG. 11.

Referring to FIGS. 13A and 13B, in one embodiment, the retainer lid 256 (FIG. 11) desirably has a length $L_6$ of about 20-25 inches and more preferably about 23.8 inches and a width $W_6$ of about 8-12 inches and more preferably about 10.34 inches. As will be described in more detail below, the retainer lid 256 is preferably snap-fit onto the distal end of the tray 254 (FIGS. 12A-12D) for securing a distal end of a medical device in the tray and for securing a retainer sleeve onto the tray. The underside of the retainer lid has molded projections 355A, 355B that engage the shaft to prevent lateral shifting of the medical device in the second channel 278 of the tray 254 (FIG. 12B).

Figure 13C:
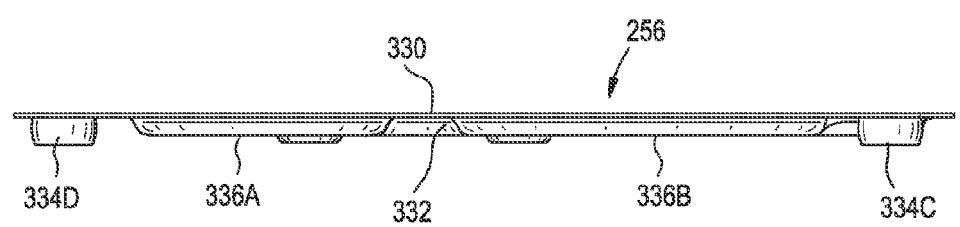
FIG. 13C shows a side elevation view of the retainer lid shown in FIG. 11.
Figure 13D:
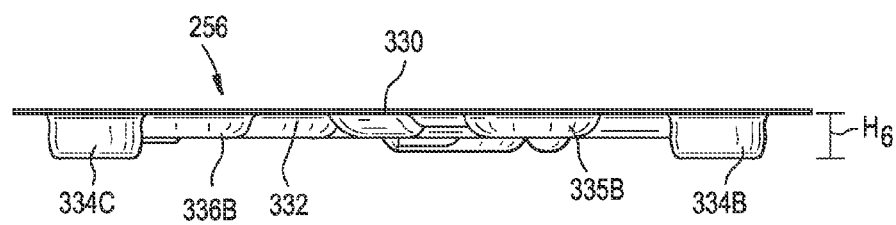
FIG. 13D shows an end elevation view of the retainer lid shown in FIG. 11.

Referring to FIGS. 13A-13D, in one embodiment, the retainer lid 256 (FIG. 11) preferably includes a top surface 330 and a bottom surface 332. In one embodiment, the retainer lid is made of polypropylene (PP). The retainer lid 256 desirably includes four snap-fit protrusions 334A-334D that project from the bottom surface 332. The retainer lid 256 desirably includes a first pair of depressions 336A, 336B that conform in size and shape to the first pair of chamber 306A, 306B on the tray 254 (FIGS. 12A and 12B) and a second pair of depressions 338A, 338B that conform to the second pair of chambers 308A, 308B on the tray 254. As shown in FIGS. 13C and 13D, the depressions 336A, 336B, 338A, 338B project from the bottom surface 332 of the retainer lid 256.

Referring to FIG. 13D, in one embodiment, each snap-fit projection 334A-334D preferably defines a height $H_6$ of about 0.300-0.350 inches and more preferably about 0.320 inches.

Figure 14:
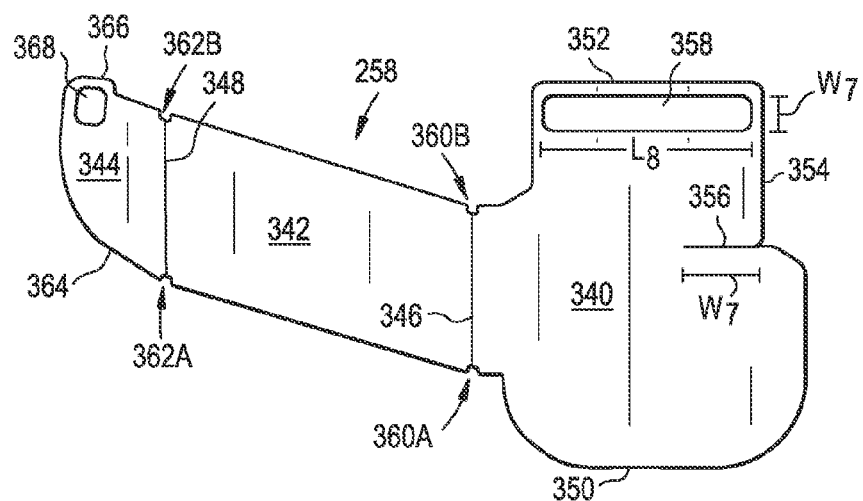
FIG. 14 shows a top plan view of the retainer sleeve shown in FIG. 11.

Referring to FIG. 14, in one embodiment, the retainer sleeve 258 (FIG. 11) preferably includes a foldable blank, such as a paperboard blank, having a top panel 340, a bottom panel 342 and a connecting panel 344. A first fold line 346 desirably extends between the top panel 340 and the bottom panel 342 for facilitating folding of the top panel and the bottom panel relative to one another. The retainer sleeve 258 desirably includes a second fold line 348 that extends between the bottom panel 342 and the connecting panel 344 for facilitating folding of the bottom panel and the connecting panel relative to one another.

In one embodiment, the top panel 340 desirably includes a proximal edge 350, a distal edge 352 and an outer edge 354. The top panel 340 desirably includes a cut 356 formed therein that extends from the outer edge 354 toward the first fold line 346. In one embodiment, the cut 356 has a length $L_3$ of about 1.50-1.75 inches and more preferably about 1.69 inches. In one embodiment, the top panel 340 includes an elongated cutout 358 that extends along the distal edge 352 thereof. In one embodiment, the elongated cutout 358 has a length $L_4$ of about 4.50-5.00 inches and more preferably about 4.81 inches and a width $W_3$ of about 0.50-1.00 inches and more preferably about 0.87 inches.

In one embodiment, a first pair of notches 360A, 360B may be provided at the ends of the first fold line 346 for facilitating folding of the top panel 340 and the bottom panel 342 relative to one another. The retainer sleeve 258 may also include a second pair of notches 362A, 362B provided at the ends of the second fold line 348 for facilitating folding of the bottom panel 342 and the connecting panel 344 relative to one another.

In one embodiment, the connecting panel 344 desirably includes a proximal edge 364 and a distal edge 366. The connecting panel preferably has a second cutout 368 formed adjacent the distal edge 366 thereof.

Figure 15A:
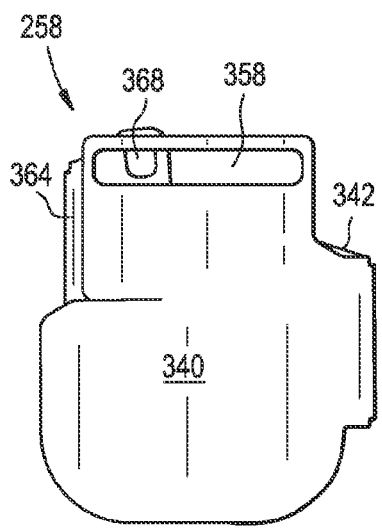
FIG. 15A shows a top view of the retainer sleeve of FIG. 14 after the retainer sleeve has been folded, in accordance with one embodiment of the present invention.
Figure 15B:
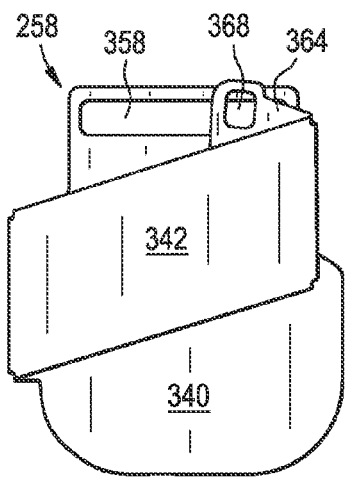
FIG. 15B shows a bottom view of the retainer sleeve of FIG. 14 after the retainer sleeve has been folded, in accordance with one embodiment of the present invention.

Referring to FIGS. 14, 15A, and 15B, in one embodiment, the retainer sleeve 258 is folded for being wrapped about the tray 254 (FIGS. 12A-12D). In one embodiment, the connecting panel 364 is preferably folded over the bottom panel 342 and the top panel 340 is folded over the connecting panel 364. After the connecting panel has been folded over the bottom panel and the top panel has been folded over the connecting panel, the elongated cutout 358 on the top panel 340 is preferably aligned with the second cutout 368 on the connecting panel 364. As will be described in more detail herein, in one embodiment, the first snap-fit projection 334A on the retainer lid (FIG. 13A) is passed through the aligned elongated cutout 358 and the second cutout 368 for securing the distal end of the retainer sleeve 258 to the tray 254 (FIG. 12A).

Figure 16A:
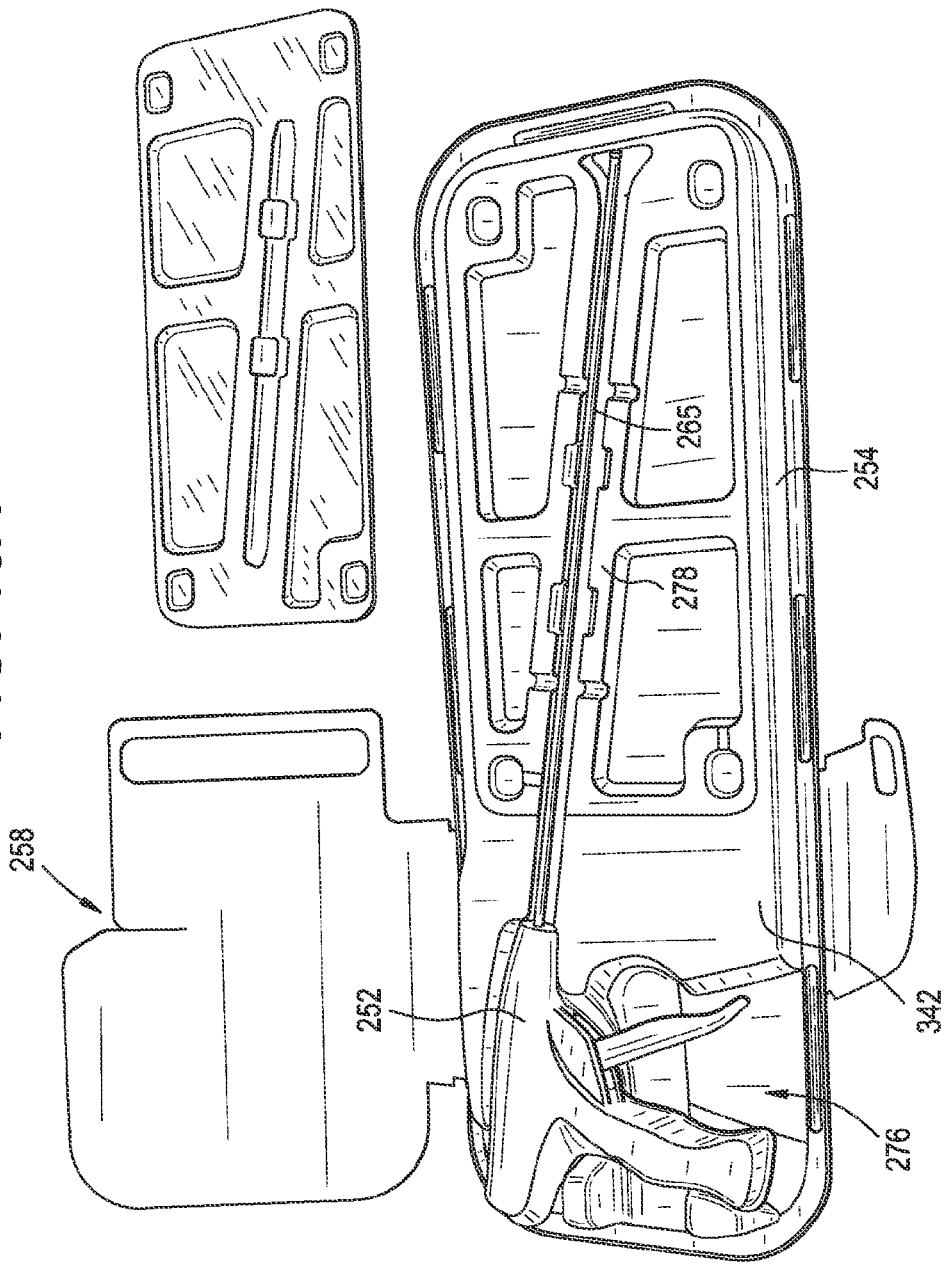
Figure 16B:
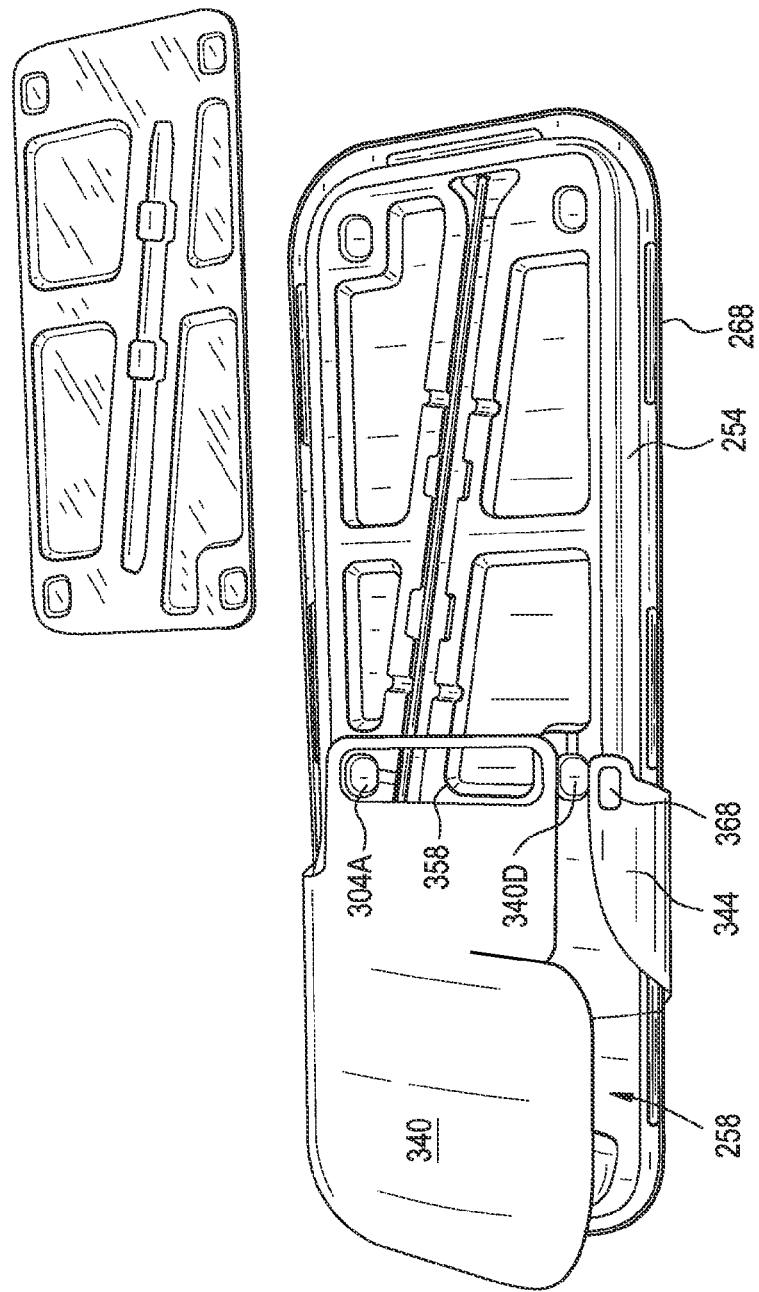

Referring to FIG. 16A, in one embodiment, the medical device 252 is disposed on the tray 254 so that the handle 252 is in the first channel 276 and the elongated shaft 265 is in the second channel 278. The bottom surface of the tray is desirably positioned over the bottom panel 342 of the retainer sleeve 258. Referring to FIG. 16B, the connecting panel 344 of the retainer sleeve 258 is folded over the second lateral edge 268 of the tray 254 so that the second cutout 368 on the connecting panel 344 overlies the fourth snap-fit depression 304D on the tray 254. Next, the top panel 340 of the retainer sleeve 258 is folded over the top surface of the tray so that the elongated cutout 358 is aligned with the first snap-fit depression 304A and the fourth snap-fit depression 304D on the tray 254. The top panel 340 preferably overlies the connecting panel 344 with the elongated cutout 358 overlying the second cutout 368, which, in turn, is aligned with the fourth snap-fit depression 304D.

Referring to FIG. 16C, after the retainer sleeve 258 has been wrapped around the tray 254, the retainer lid 256 is preferably secured to the distal end of the top surface of the tray 254 with the four snap-fit projections 334A-334D (FIG. 13C) on the retainer lid 256 inserted into the corresponding four snap-fit depressions 304A-304D formed on the tray 254. When the retainer lid 256 has been secured to the tray 254, the first snap-fit projection 334A on the retainer lid passes though the elongated slot 358 and into the first snap-fit depression 304A on the tray. In addition, the fourth snap-fit projection 334D of the retainer lid 256 passes through the elongated cutout 358 of the top panel 340, the second cutout 368 of the connecting panel 344, and is secured by the fourth snap-fit depression 304D for securing the retainer sleeve 258 over the proximal end of the tray 254. After the retainer sleeve 258 has been secured over the proximal end 262 of the tray 254, the top panel 340 of the retainer sleeve 258 overlies the top surface of the tray at the proximal end 262 of the tray 254. The cut 356 provided in the top panel 340 enables a free edge of the top panel 340 to flex away from the top surface of the tray 254 for accessing the medical device stored on the tray.

Referring to FIG. 16D, in one embodiment, after the retainer sleeve 358 has been secured to the tray 254, the retainer sleeve wraps around the tray so that the bottom panel 342 of the retainer sleeve overlies the bottom surface 274 of the tray 254.

Figure 16E:
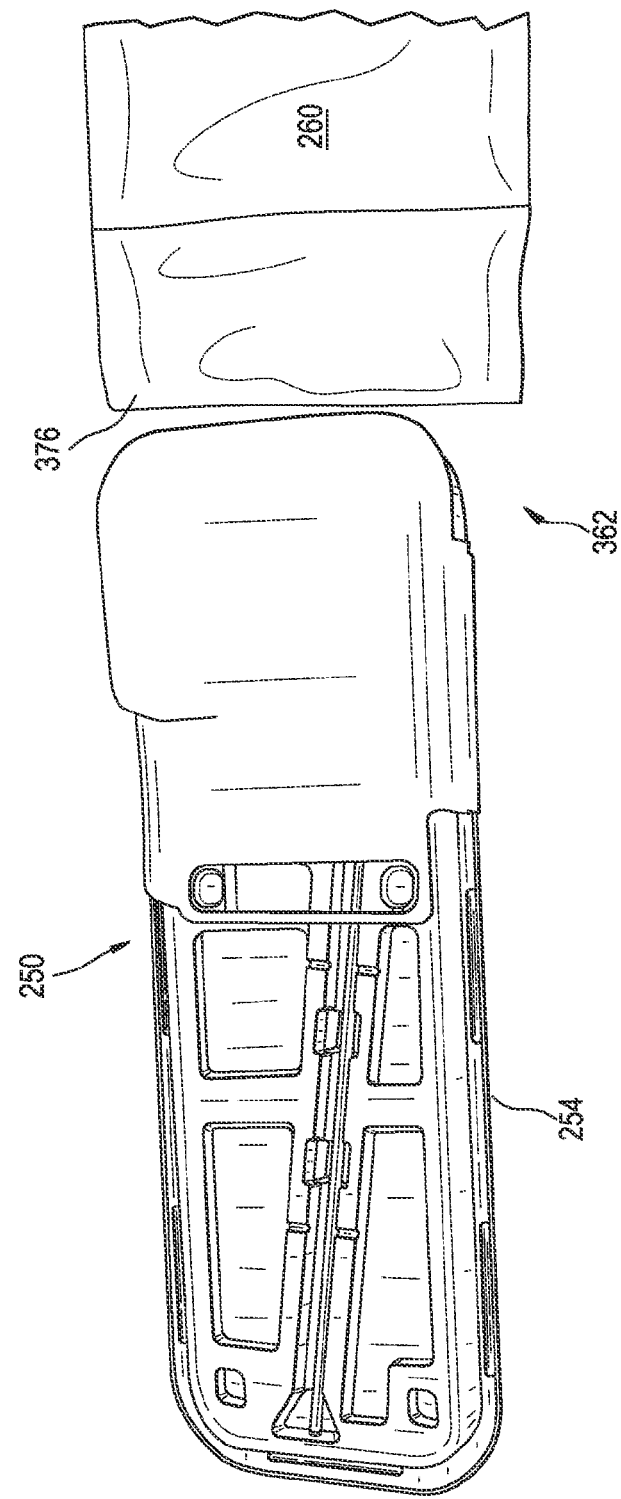

Referring to FIG. 16E, in one embodiment, the proximal end 362 of the tray 254 of the package 250 is inserted into an open end 376 of the outer pouch 260. FIG. 16F shows the tray 254 of the package 250 after it has been further inserted into open end 376 of the outer pouch 260. FIG. 16G shows the outer pouch 260 after the multi-component package has been fully inserted therein.

In one embodiment, the outer pouch 260 preferably includes a first sealed lateral edge 370, a sealed distal edge 372 and a second sealed lateral edge 374. The outer pouch 260 also includes the open, unsealed proximal edge 376 that enables the interior of the pouch and the package loaded therein to be sterilized using EtO gasses that are circulated throughout the interior of the pouch 260 and around the tray and the medical device. Once the interior of the pouch and the package have been sterilized using EtO gasses, the open proximal end 376 may be sealed for completely sealing the package within the outer pouch 260. A corner of the sealed pouch 260 desirably includes a corner opening tab 378 that may be peeled apart for opening the sealed pouch and accessing the medical device loaded onto the tray.

Referring to FIG. 17A, in one embodiment, a package 450 for a medical device 452 preferably includes a tray 454 adapted to receive the medical device 452, a retainer lid 456 that is snap-fit onto a distal end of the tray 454, and a cover flap 458 that is attached to one lateral side of the tray 454 and that is secured to the top surface of the tray 454 by the retainer lid 456. The assembled package 450 may be inserted into an open end of a sealable outer pouch, such as a foil pouch.

In one embodiment, the tray 454 of the package desirably includes a proximal end 462, a distal end 464, a first lateral side 466, and a second lateral side 468. The tray 454 preferably has a peripheral outer flange 470 that extends around the outer perimeter of the tray.

In one embodiment, the cover flap 458 preferably includes a paperboard blank having a top panel 540 with a lateral edge 546 that is preferably attached to the second lateral side 468 of the tray for forming a closed side of the cover flap 458 that extends along the second lateral side 468 of the tray.

In one embodiment, the cover flap 458 desirably includes a proximal edge 550, a distal edge 552, an outer edge 554, and the lateral edge 546. The cover flap 458 desirably includes a cut 556 formed therein that extends from the outer edge 554 toward the lateral edge 546. In one embodiment, the cover flap 458 preferably includes an elongated cutout 558 that extends along the distal edge 552 thereof.

Figure 17B:
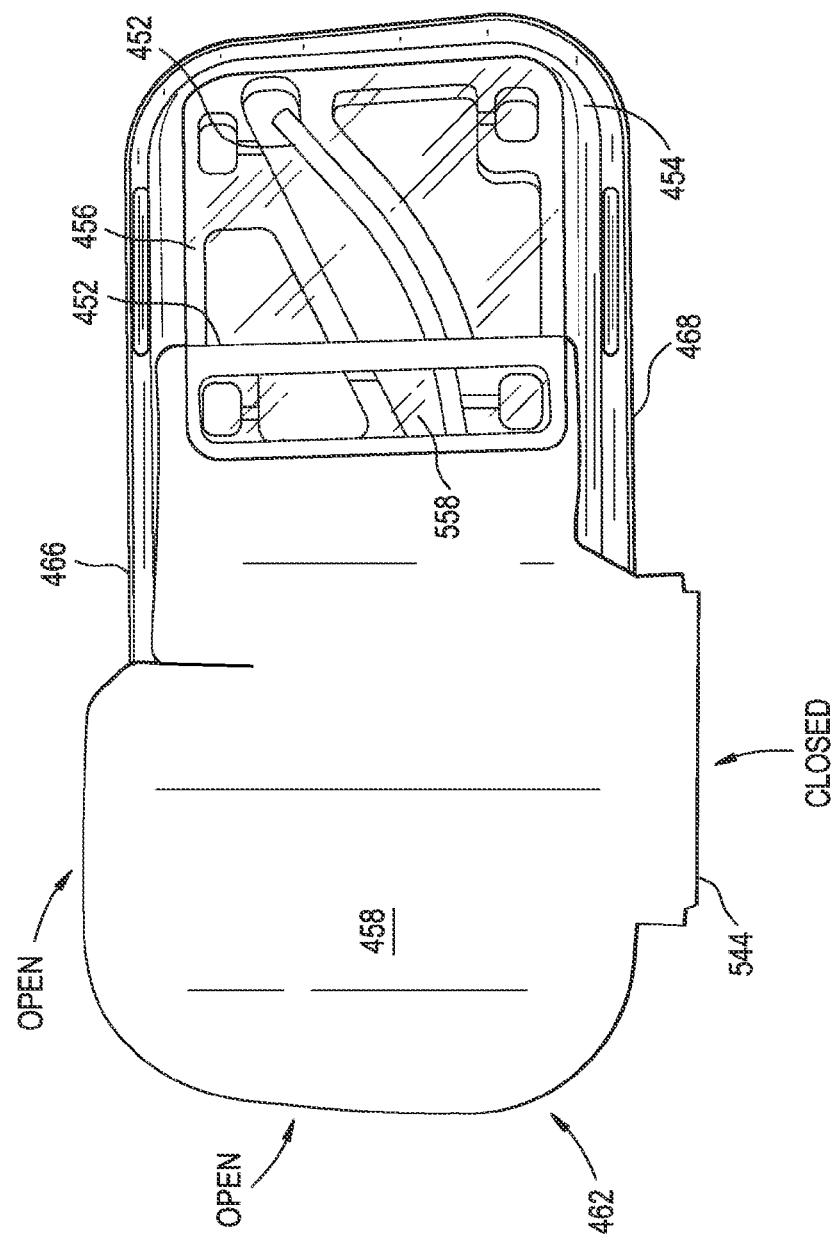
FIG. 17B shows the package of FIG. 17A with the cover flap secured to a second lateral side of the tray and secured over the top surface of the tray by the retainer lid, in accordance with one embodiment of the present invention.

Referring to FIGS. 17A and 17B, in one embodiment, the cover flap 458 desirably covers the top surface of the tray 454 at the proximal end of the tray. The lateral edge 546 of the cover flap is preferably secured to the second lateral edge 468 of the tray 454 (e.g., by a securing element) to form a closed side of the cover flap. One or more of the projections on the retainer lid 456 desirably pass through the elongated slot 558 on the cover flap 458 for securing the distal end 552 of the cover flap 458 to the top surface of the tray 454. When secured to the tray 454, the cover flap 458 has a closed side that extends along the second lateral side 468 of the tray, a first open side that extends along the proximal edge 462 of the tray, and a second open side that extends along the first lateral edge 466 of the tray 454. The cover flap 458 is preferably flexed away from the top surface of the tray for accessing the medical device 452. As the handle of the medical device is rotated away from the top surface of the tray, the first and second open sides of the cover flap 458 preferably move away from the top surface of the tray 454 to allow for removal of the medical device 452 from the tray, such as shown and described herein (e.g., in FIGS. 10A-10B).

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A package for a medical device comprising:
  a tray having a top surface, a bottom surface, a proximal end, a distal end, and first and second lateral sides that extend between the proximal and distal ends, wherein the proximal end of said tray includes a first channel adapted to receive a handle of a medical device;
  said tray having elements projecting from said top surface;
  a retainer lid secured to said tray for covering said top surface of said tray at the distal end of said tray, wherein said retainer lid does not cover the proximal end of said tray that includes said first channel;
  a retainer sleeve having a distal end and a proximal end, the distal end of said retainer sleeve being wrapped around said top and bottom surfaces of said tray and being secured to said tray by said retainer lid, the proximal end of said retainer sleeve including a top panel that covers said top surface of said tray at the proximal end of said tray, wherein said top panel of said retainer sleeve covers the proximal end of said tray that includes said first channel that is not covered by said retainer lid, and wherein said top panel of said retainer sleeve has a free edge that is adapted to flex away from said top surface of said tray.

2. The package as claimed in claim 1, wherein said retainer sleeve comprises a cut that extends between said free edge of said top panel and the distal end of said retainer sleeve for enabling said free edge of said top panel to move relative to the distal end of said retainer sleeve.

3. The package as claimed in claim 1, wherein said elements projecting from said top surface of said tray are molded elements that define said first channel at the proximal end of said tray, a second channel distal to said first channel that extends toward the distal end of said tray, and at least one retaining element located at the proximal end of said tray.

4. The package as claimed in claim 3, wherein said at least one retaining element comprises a pair of retainer posts that are spaced from one another at the proximal end of said tray.

5. The package as claimed in claim 4, wherein said molded elements further comprise a mound located between said first and second channels, wherein said mound has a top surface including a flat proximal section and a sloping distal section that slopes downwardly toward the distal end of said tray.

6. The package as claimed in claim 5, wherein said first and second channels intersect one another at said mound.

7. The package as claimed in claim 6, wherein said first and second channels define recesses molded into said tray and said mound projects above said first and second channels.

8. The package as claimed in claim 7, wherein said mound has a proximal face that opposes said first and second retainer posts.

9. The package as claimed in claim 8, wherein said top surface of said tray further comprises a central depression that extends between the proximal edge and said proximal face of said mound, and wherein said central depression is located between said first and second retainer posts.

10. The package as claimed in claim 9, further comprising a medical device having a handle and an elongated shaft extending from said handle, wherein said handle is disposed in said first channel of said tray and said elongated shaft is disposed in said second channel of said tray.

11. The package as claimed in claim 10, wherein said top panel of said retainer sleeve covers said handle of said medical device, and wherein said cut of said retainer sleeve enables said free edge of said top panel to be flexed away from said handle and said top surface of said tray to allow removal of said medical device from said tray.

12. The package as claimed in claim 10, wherein said top surface of said tray has one or more snap-fit depressions molded therein at the distal end of said tray and said retainer lid has one or more snap-fit projections molded therein that extend from a bottom surface thereof, and wherein said one or more snap-fit projections of said retainer lid are insertable into said one or more snap-fit depressions of said tray for securing said retainer lid to said tray.

13. The package as claimed in claim 12, wherein the distal end of said retainer sleeve comprises one or more cutouts that are aligned with at least one of said one or more snap-fit depressions molded in said tray, and wherein at least one of said one or more snap-fit projections on said retainer lid pass through said one or more cutouts for securing the distal end of said retainer sleeve to said tray.

14. The package as claimed in claim 13, wherein said retainer sleeve comprises:
a bottom panel that covers said bottom surface of said tray;
said top panel attached to a first edge of said bottom panel; and
a connecting panel attached to a second edge of said bottom panel, wherein said retainer sleeve wrapped around said tray covers said first and second lateral sides of said tray.

15. The package as claimed in claim 1, wherein said tray comprises high-density polyethylene (HDPE), said retainer lid comprises polypropylene (PP) and said retainer sleeve comprises paperboard.

16. The package as claimed in claim 1, wherein said tray is thicker at the proximal end and thinner at the distal end.

17. The package as claimed in claim 1, further comprising an outer pouch adapted to receive said tray, said retainer lid and said retainer sleeve, wherein said outer pouch is sealable for forming an air-tight seal.

18. The package as claimed in claim 1, wherein said tray comprises a peripheral flange that extends around the outer perimeter of said tray, and wherein said top surface of said tray is above said peripheral flange and said bottom surface of said tray is below said peripheral flange.

19. A package for a medical device comprising:
a thermoformed tray having a top surface, a bottom surface, a proximal end, a distal end, and first and second lateral sides that extend between the proximal and distal ends;
a medical device disposed over said top surface of said tray, said medical device having a handle overlying the proximal end of said tray and an elongated shaft projecting distally from said handle;
said tray having elements projecting from said top surface including a first channel for receiving said handle, a second channel for receiving said elongated shaft, a mound located between said first and second channels, and a pair of retainer posts located at the proximal end of said tray, wherein said handle is disposed between said retainer posts and said mound for minimizing proximal and distal movement of said medical device relative to said tray;
a thermoformed retainer lid secured to said tray for covering said elongated shaft of said medical device at the distal end of said tray, wherein said retainer lid does not cover the proximal end of said tray and said handle of said medical device;
a retainer sleeve having a distal end and a proximal end, the distal end of said retainer sleeve being wrapped around said tray to cover said top and bottom surfaces of said tray, the distal end of said retainer sleeve being secured to said tray by said retainer lid, and the proximal end of said retainer sleeve including a top panel that covers said top surface of said tray at the proximal end of said tray, wherein said top panel of said retainer sleeve covers the proximal end of said tray and said handle of said medical device that is not covered by said retainer lid, wherein said top panel of said retainer sleeve has a free edge that is adapted to flex away from said top surface of said tray to provide access to said handle of said medical device, wherein said handle has a base and said handle is pivotable about said base to clear said handle of said retainer posts so that said medical device is moveable in a proximal direction to remove said medical device from said tray.

20. The package as claimed in claim 19, wherein said thermoformed tray comprises high-density polyethylene (HDPE), said thermoformed retainer lid comprises polypropylene (PP), and said retainer sleeve comprises paperboard.

21. The package as claimed in claim 19, wherein said elements projecting from said top surface of said tray are molded elements.

22. A package for a medical device comprising:
a tray having a top surface, a bottom surface, a proximal end, a distal end, and first and second lateral sides that extend between the proximal and distal ends, wherein the proximal end of said tray includes a first channel formed in the top surface that is adapted to receive a handle of a medical device;
said tray having elements projecting from said top surface;
a retainer lid secured to said tray for covering said top surface of said tray at the distal end of said tray;
a cover flap having a proximal end, a distal end, and a lateral side extending between the proximal and distal ends, the lateral side of the cover flap being secured to one of the lateral sides of said tray and the distal end of said cover flap being secured to said tray by said retainer lid, wherein said retainer lid does not cover said first channel at the proximal end of said tray and said cover flap covers said first channel at the proximal end of said tray that is not covered by said retainer lid, and wherein said cover flap has a free edge that is adapted to flex away from said top surface of said tray.

\* \* \* \* \*